United States Patent
Rahman et al.

(10) Patent No.: US 11,065,211 B2
(45) Date of Patent: Jul. 20, 2021

(54) ISOXYLITONES MEDIATED NEUROGENESIS

(71) Applicants: Atta-ur- Rahman, Karachi (PK); Muhammad Iqbal Choudhary, Karachi (PK); Farzana Shaheen, Karachi (PK); Shabana Usman Simjee, Karachi (PK); Saba Majeed, Karachi (PK); Anila Bashir, Karachi (PK); Kanwal Iftikhar, Karachi (PK)

(72) Inventors: Atta-ur- Rahman, Karachi (PK); Muhammad Iqbal Choudhary, Karachi (PK); Farzana Shaheen, Karachi (PK); Shabana Usman Simjee, Karachi (PK); Saba Majeed, Karachi (PK); Anila Bashir, Karachi (PK); Kanwal Iftikhar, Karachi (PK)

(*) Notice: Subject to any disclaimer, the term of this patent is extended or adjusted under 35 U.S.C. 154(b) by 91 days.

(21) Appl. No.: 15/934,539

(22) Filed: Mar. 23, 2018

(65) Prior Publication Data
US 2019/0290598 A1 Sep. 26, 2019

(51) Int. Cl.
*A61K 31/12* (2006.01)
*A61P 25/28* (2006.01)

(52) U.S. Cl.
CPC .............. *A61K 31/12* (2013.01); *A61P 25/28* (2018.01)

(58) Field of Classification Search
CPC ................................. A61K 31/12; A61P 25/28
See application file for complete search history.

(56) References Cited

U.S. PATENT DOCUMENTS 5,972,883 A * 10/1999 Gozes .............. C07K 14/57563
514/21.5
7,399,888 B2 * 7/2008 Rahman ................ C07C 45/004
568/377

OTHER PUBLICATIONS

Demars et al. Journal of Neuroscience Research 88:2103-2117 (2010) (Year: 2010).*
Gao et al. Nat Neurosci. 12(9): 1090-1092 (2009) (Year: 2009).*
O'Sullivan et al. Movement Disorders, 26(1), 45-50 (2011) (Year: 2011).*

* cited by examiner

*Primary Examiner* — Dennis Heyer
(74) *Attorney, Agent, or Firm* — Sarfaraz K. Niazi

(57) ABSTRACT

This invention provides an effective method and a composition for treating neurodegenerative diseases and conditions of the central and peripheral nervous system by stimulating neurogenesis by the use isoxylitones or an isomer, acid analog, a salt or a solvate, thereof.

4 Claims, 19 Drawing Sheets

A

B

A

B

ISOXYLITONES MEDIATED NEUROGENESIS

FIELD OF THE INVENTION

This invention relates to methods and compounds for treating neurodegeneration by stimulating neurogenesis through administration of isoxylitones or an isomer, acid analog, a salt or a solvate, thereof.

BACKGROUND OF THE INVENTION

Neurogenesis refers to the birth or production of new neurons in brain that includes cell division, migration, proliferation and survival of new cells. The capacity of the adult brain to generate new neurons has been discussed many times over last four decades. Initially it was reported that neurogenesis occurs during early development of brain and once neural circuit/structure has completed, the regeneration of neurons gets stopped except discrete regions in sub ventricular zone (SVZ) and dentate gyrus (DG) regions of hippocampus.

It was first revealed by Altman that in an adult brain some dividing cells survived and differentiated into neuronal like cells using triturated thymidine autoradiography. In the early 1990's, it was reported that with different culture conditions, extrinsic, and intrinsic factors neural progenitor cells (NPCs) can be isolated and differentiated into glia and mature neurons. In adult mammalian brain, cell genesis occurs specifically in two neurogenic areas i.e., in SVZ of lateral ventricles and in sub-granular zone (SGZ) of hippocampal dentate gyrus.

In SVZ, progenitor cells migrate through rostral migratory stream into olfactory bulb giving rise to granule cells which differentiated into interneurons. A multipotent stem cells resides mostly in forebrain lateral ventricles of mammalian brain, these NPC's can produce multiple cell types in nervous system such as neurons, astrocytes and oligodendrocytes. Rare neurogenesis has been reported in cortical, amygdala, hypothalamus and substantial niagra.

The hippocampal neurogenesis has been studied extensively for its role in learning, memory and cognitive behavior. Hippocampal neurogenesis can be utilized as a therapeutic target for depression and psychiatric diseases. Some studies have also revealed that neurodegeneration of hippocampal neurons after chronic exposure to stress affecting hippocampal viability and the stress induced reduction in hippocampal volume can be reversed. The clinical data has revealed that antidepressant drugs stimulates neurogenesis by activation of second messenger system which activates transcription and neurotrophic factors resulting in increased no of neurons.

Adult neurogenesis can be influenced by a broad range of hormones, drugs, extrinsic/intrinsic factors, physical exercise and particularly drugs used for treating neurodegeneration and neuropsychiatric disorders such as depression. Recently it has been shown that intracerebral infusion of EGF and FGF-2 in rats increased proliferation in SVZ region but no proliferation reported in SGZ by both factors. Studies have reported that glucocorticoid and stress reduces cell genesis in hippocampus through downstream effect on NMDA receptors. Neurotransmitters have also been shown to be involved in neurogenesis i.e. glutamate receptor antagonist MK-801 enhances proliferation while glutamate analogs reduce cell division in dentate gyrus of hippocampus.

The existence of neural progenitor cells in adult CNS has opened a new advent of research to explore the potential of these cells for treatment of neurodegenerative disorders like AD, dementia, Parkinson's disease, multiple sclerosis and to some extent stroke or epilepsy which trigger neuronal damage. There are some important transcription factors, like NeuroD1 (ND1) and neurogenin (are the members of the basic helix-loop-helix) (bHLH) family in relation with other members implicated in the regulation of neurogenesis. The ND1 has previously been used as a marker for neuronal precursor cells and as a corresponding gene for induction and differentiation of neurogenesis.

However, little is known about the exact role of ND1 and neurogenin in neural progenitor cells (NPCs) differentiation and in neuronal fate choice. Neurogenins have a crucial role in neurogenesis and in specifying neuronal differentiation. The increased expression of neurogenin exhibits amplification of pro neural genes and determine neural fate by reducing expression of glial genes in neural progenitor cells (NPCs) that further differentiates into neurons expressing tubulin and calbindin. Therefore, new therapeutic advances are required to implicate the approach of modulation and regeneration of neurons to compensate neuronal loss and deficits related to neurological diseases by novel neurogenic drugs.

To date, no drugs are available that can effectively cure the CNS disorders associated with neurodegeneration such as stroke, Alzheimer's disease, Parkinson disease, ischemic induced neurodegenerations. Hence, there is an urgent need to develop better treatment strategies for these disorders, particularly focused on novel compounds involve in up-regulation of neurogenesis. The existence of neural precursor cells in adult CNS has opened a novel dimension of research to explore the potential of these cells for treatment of neurological disorders. The present invention is a result of investigation into surprising neurogenic potential of isoxylitones in cortical and hippocampal neonatal cultures and these small molecules isoxylitones act as modulators that can augment the physiological neurogenesis.

Novel approach was developed for the analysis of neurogenesis using cocultured cells where the marked up-regulation of neurogenic transcriptional program (NeuroD1 and Ngn-2) was observed by successful generation of differentiating BMSCs into neurons confirmed by the increased in expression of neuronal markers (tubulin and CR). We also observed that isoxylitones is capable of differentiating more hippocampal cells into neuronal-like lineage as compared to the cocultured cells.

U.S. Pat. No. 7,399,888 describes isoxylitones identification from medicinal plants as an anticonvulsant agent. The patent also covers the detailed antiepileptic activity and chronic toxicity studies of isoxylitones. Citation of the above document is not intended as an admission that any of the foregoing is pertinent prior art.

DETAILED DESCRIPTION OF THE INVENTION

Figure 1:
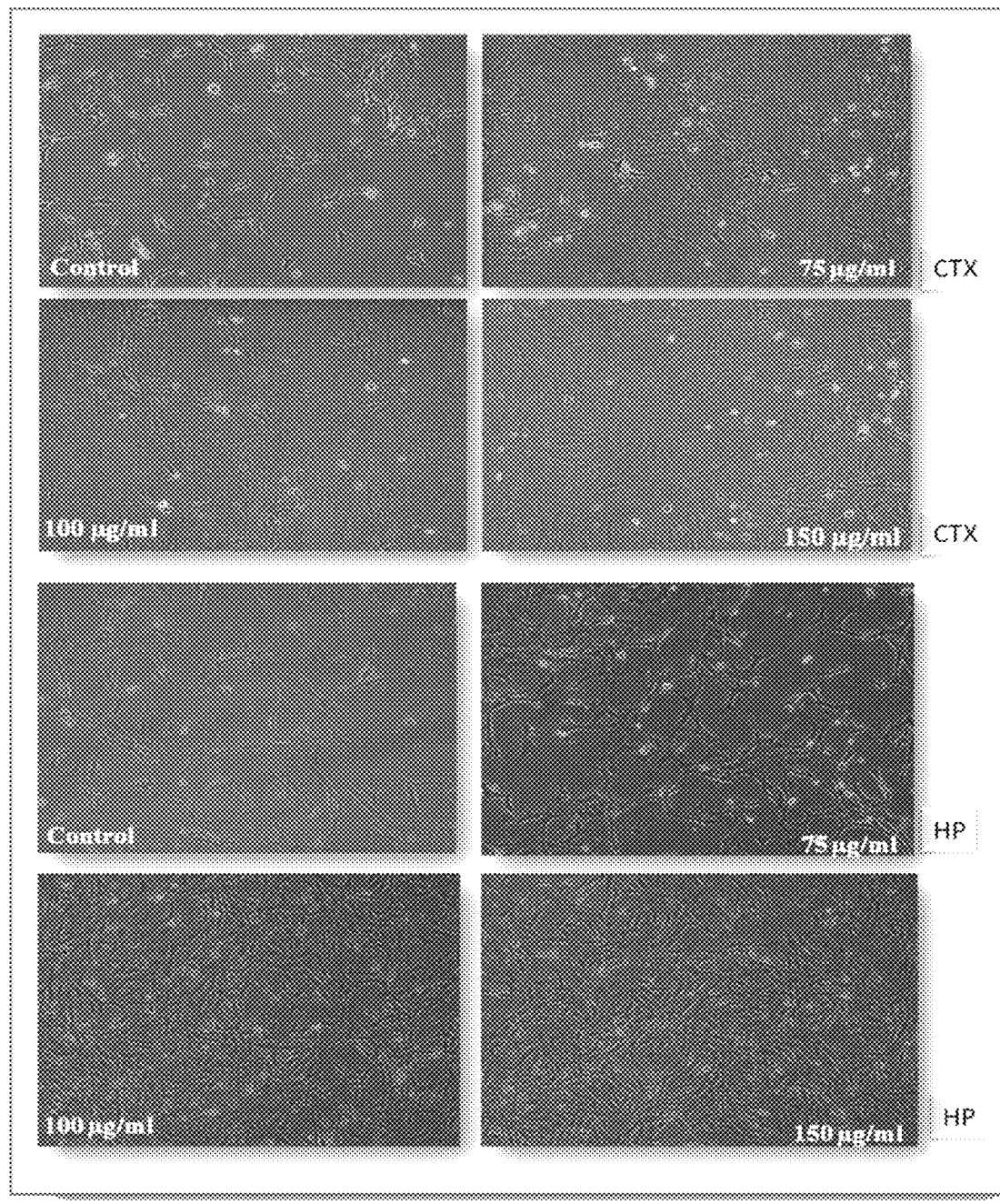
FIG. 1 depicts a representative phase contrast photomicrographs showing the effect of isoxylitones on morphology of cortical (CTX) and hippocampal (HP) cells treated for 24 h. An increased proliferation can be seen in cells exposed to the claimed compounds without any significant change in morphology. The treated hippocampal cells demonstrated higher proliferation as compared to cortical cells. Experiments were carried out at least three times and representative sections are shown at original magnification i.e., 10×.
Figure 2:
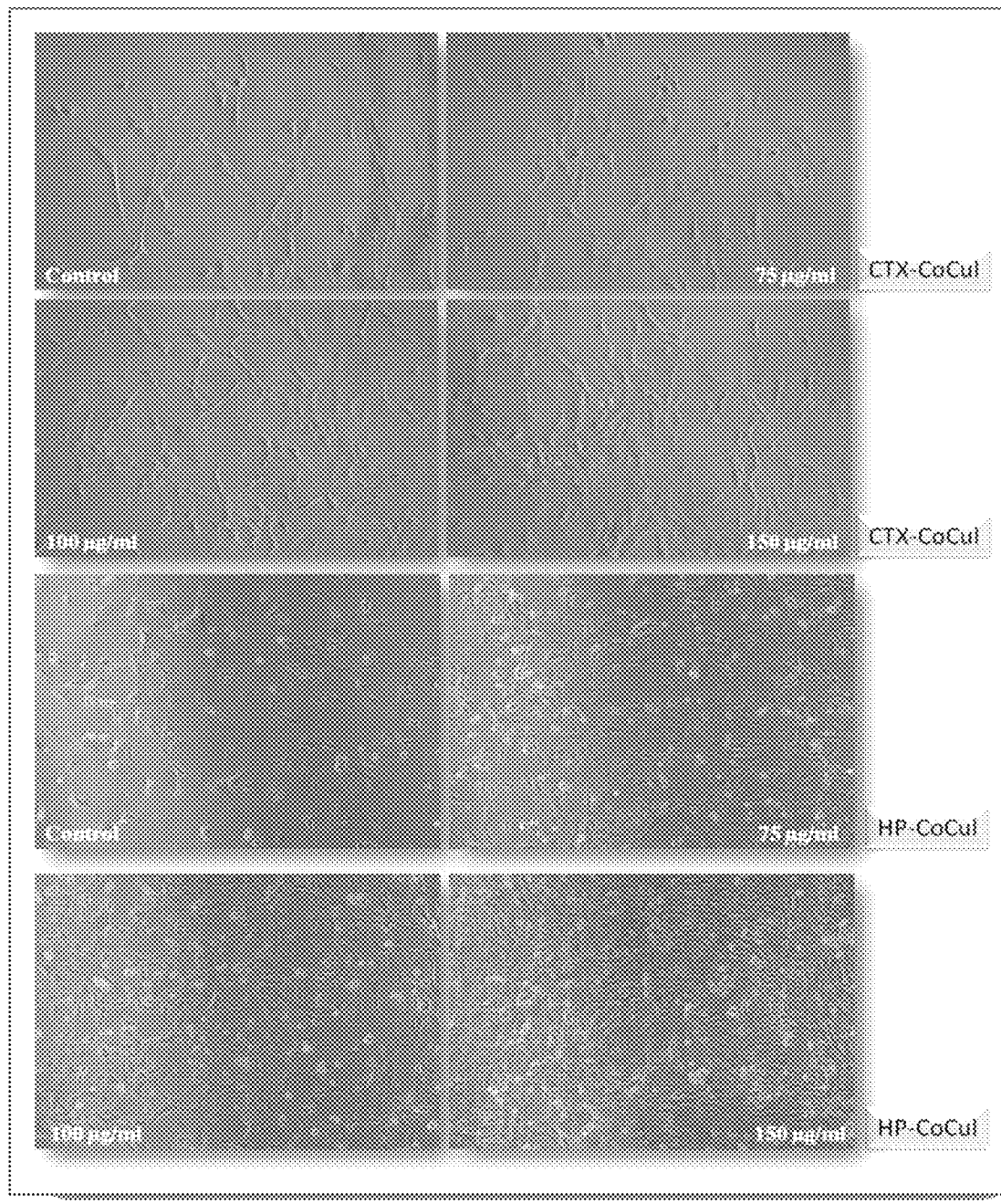
FIG. 2 depicts a co-cultured cortical (CTX-CoCul) and hippocampal (HP-CoCul) cells with and without treatment with isoxylitones for a period of 24 h. Marked increase in the number of proliferating cells was observed with isoxylitones treatment with no significant variation in the morphology. However, it was interesting to note the rate of proliferation was almost double in the hippocampus cells as compared to the cortical cells (magnification 10×).
Figure 3:
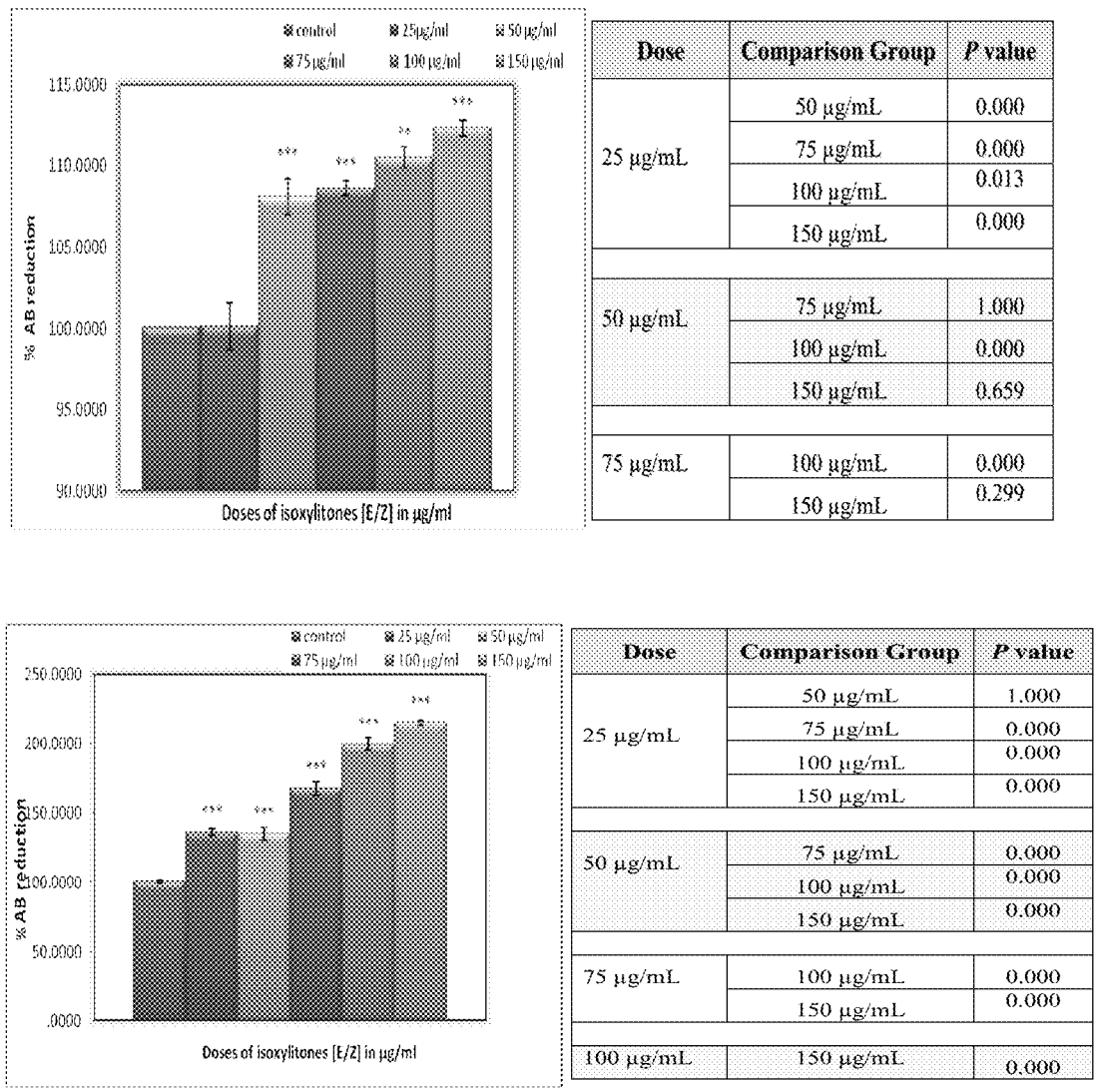
FIG. 3 depicts a proliferation of the cortical and hippocampal cells following 24 h treatment with isoxylitones. Alamar blue assay was performed. Isoxylitones exhibited the growth supportive and proliferative effect on both cortical and hippocampal cells. Significant difference between control and isoxylitones treated cells was observed and is indicated by *P<0.001 and P<0.05. Each bar represents mean±S.E.M of three independent experiments. The level of significance within the test groups are given in the table illustrated under the bar diagram.
Figure 4:
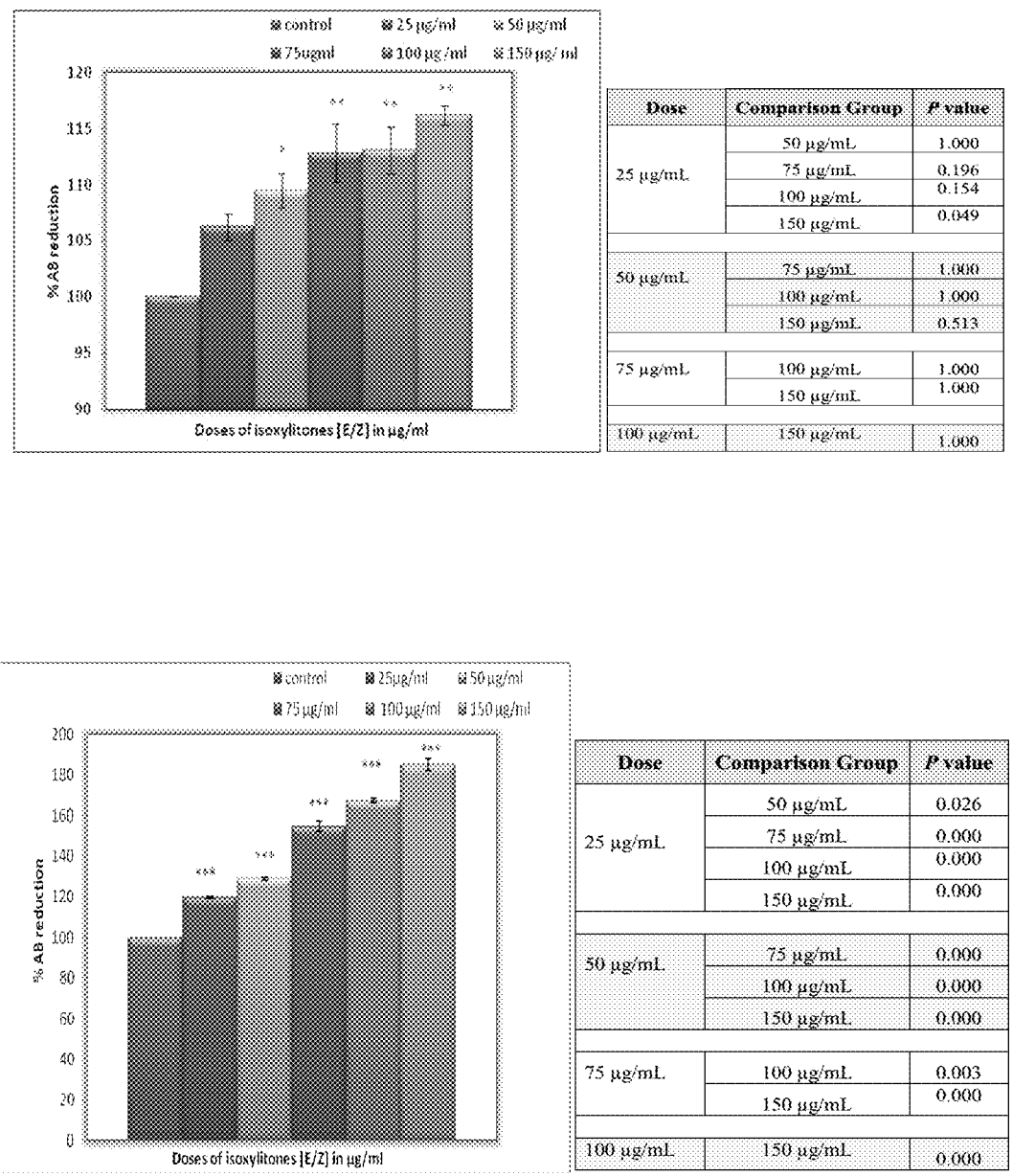
FIG. 4 depicts a growth proliferations of Cocul-CTX and Cocul-HP cells after 24 h treatment with isoxylitones. Each bar represents mean±S.E.M of three separate experiments. Cells were treated with various doses of the test compound and latter Alamar blue assay was performed. A dose dependent growth proliferative effect of the treatment was observed with highest proliferative dose of 150 µg/ml. A significant difference was analyzed when the isoxylitones treated groups were compared with the control and it is indicated by **P<0.001 and *P<0.05. The table under the bar diagram shows the difference within the test groups.
Figure 5:
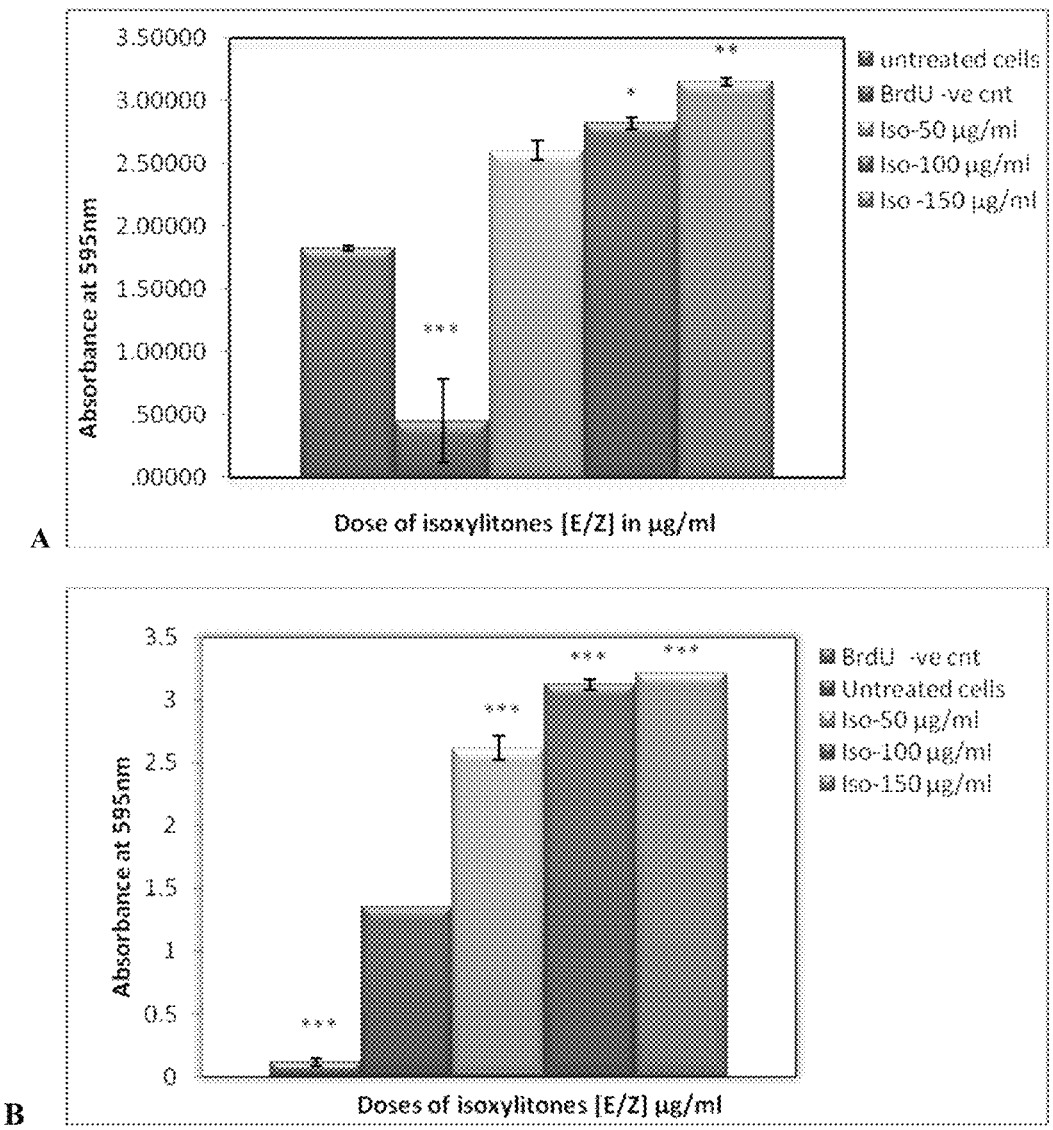
FIG. 5 depicts a BrdU positive (A) cortical cells and (B) hippocampal cells following treatment with isoxylitones. Cells were treated with various concentrations of isoxylitones for 24 h and BrdU proliferation ELISA assay was performed. Significant increase in BdrU positive cells proliferation was observed when isoxylitones (100 µg/mL) and (150 µg/mL) was used. Each bar represents mean±S.E.M of three independent experiments. One-way ANOVA reveals a significant difference between control cells and the hippocampal cells receiving treatment of isoxylitones (*P<0.001). Whereas significant difference between control and treatment groups of cortical cells is indicated by *P<0.001. The results show that isoxylitones significantly increased BrdU positive cells in hippocampal cells at 100 and 150 µg/ml and slightly increased BrdU positive cells in cortical cells when given at 150 µg/ml.
Figure 6:
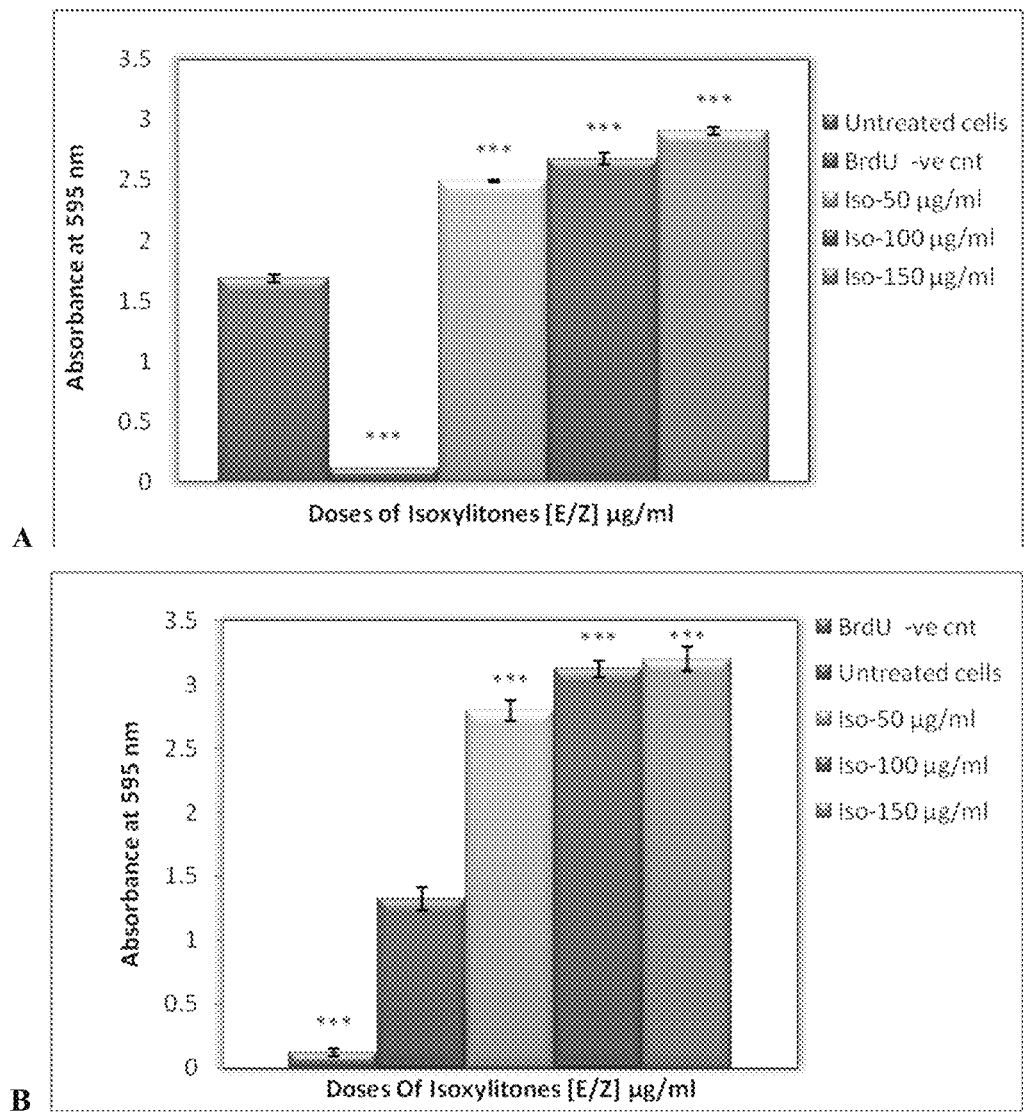
FIG. 6 depicts BrdU labeled (A) cocultured cortical cells and (B) cocultured hippocampal cells treated with isoxylitones. Following 24 h treatment with isoxylitones of both cultured cells, BrdU proliferation ELISA assay was performed. BdrU labeled cells significantly increased when isoxylitones (100 µg/mL) and (150 µg/mL) was used. One-way ANOVA reveals a significant difference between control cells and the cocultured hippocampal cells after treatment of isoxylitones (*P<0.001). A significant difference between control and treatment groups of CoCul-CTX cells is indicated by *P<0.001. The results indicate that isoxylitones significantly elevated the BrdU positive cells in CoCul-HP cells and also increased BrdU positive cells in CoCul-CTX cells when given at 150 µg/ml. Each bar shows mean±S.E.M of three individual experiments.
Figure 7:
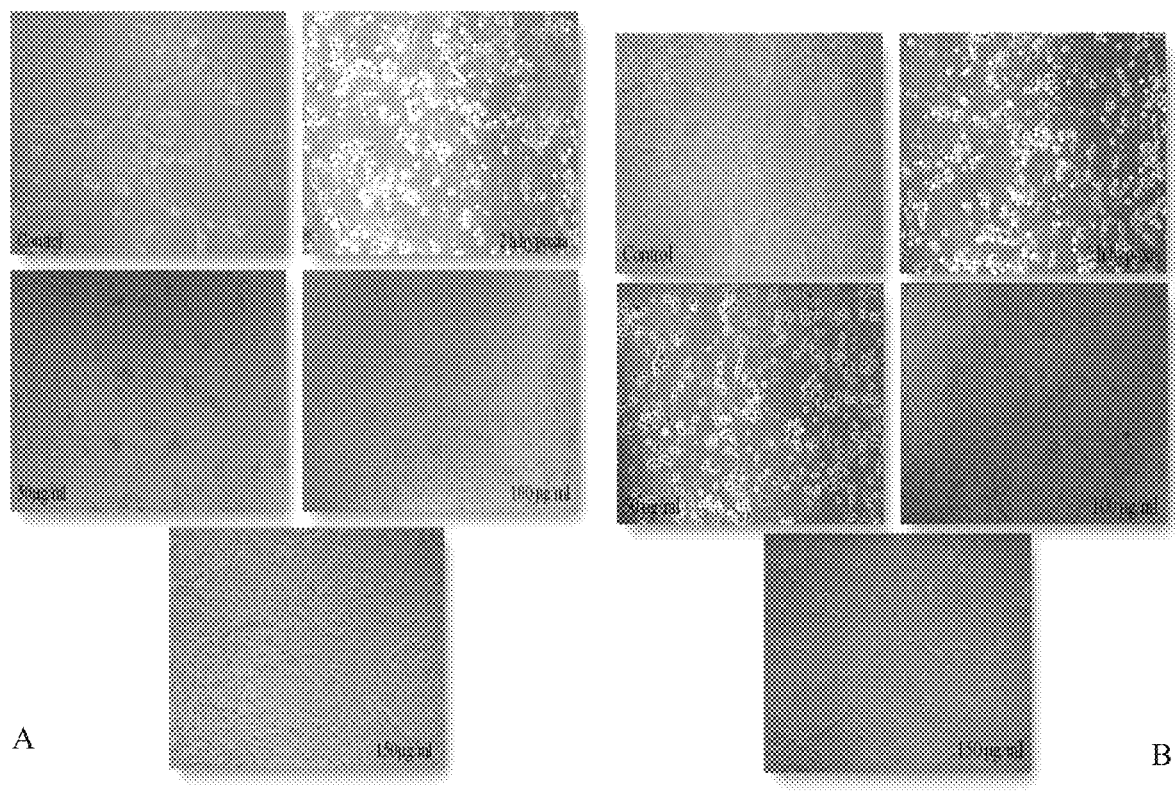
FIG. 7 depicts Hypoxic cortical cells treated with isoxylitones over a period of 48 h. (A) Representative images of cortical cells and (B) hippocampal cells showing 48 h treatment with isoxylitones after 2 hrs hypoxia; Cells were kept under hypoxic conditions for 2 h and following hypoxia, treatment was given at various concentrations of isoxylitones for 24 h. Images were visualized by phase-contrast microscopy. The morphology of hypoxic cells revealed loose and shrunken cells. Some of the cells were fractured and cotton-shaped. Recovery of hypoxic cells clearly observed in treatment groups in comparison to the positive control hypoxic cells. Experiments were carried out at least three times and representative sections are shown at original magnification i.e., 10×.
Figure 8:
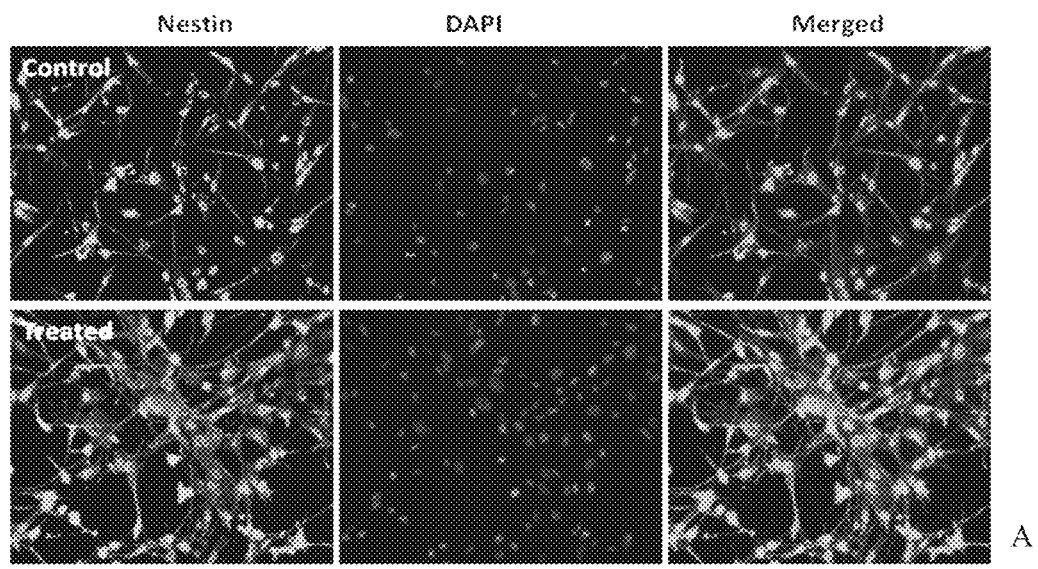
FIG. 8 depicts immunofluorescence images showing nestin expression in (A) hippocampal and (B) CoCul-HP cells after treatment with isoxylitones. HP and cocultured cells were treated with 150 µg/ml isoxylitones Following 24 h treatment, immunostaining was performed to and intensity of the fluorescence was analyzed to determine the expression of nestin. Images were analyzed using ImageJ software. Blue staining reflects the DAPI that stains the cell nucleus. Arrow in the treated image clearly shows the up-regulation of nestin protein expression in the treated cells as compared to untreated control.
Figure 8:
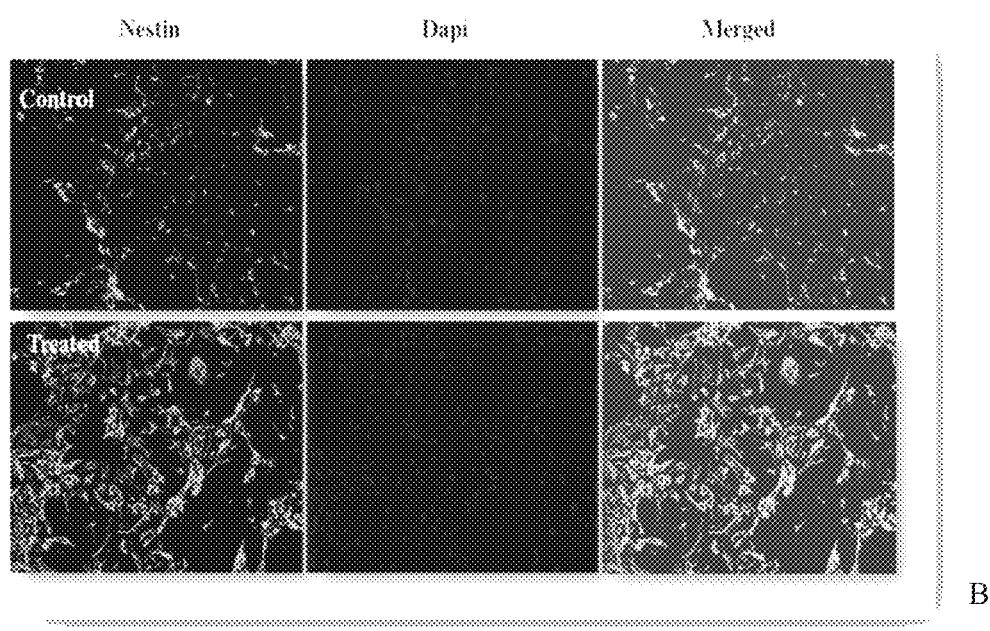
Figure 9:
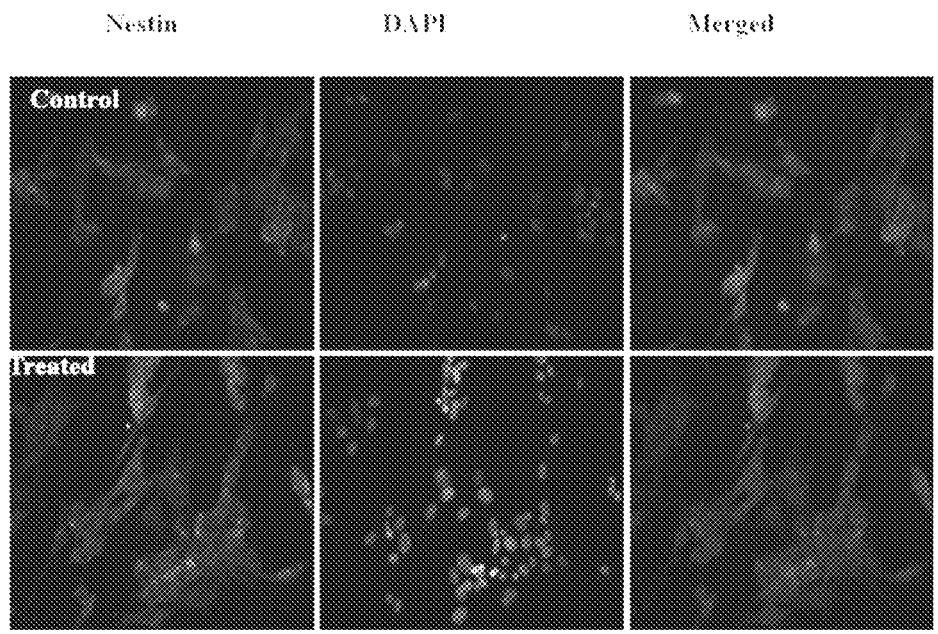
FIG. 9 depicts Nestin positive (A) CTX and (B) CoCul-CTX cells following treatment with isoxylitones. Representative images shows expression of nestin in cortical cells following 24 h treatment with isoxylitones. Slight increased in the nestin expression of the treated cells can be spotted in the images as compared to the control group, however statistical analysis revealed no significant difference. Images were captured using 90i microscope at 20× magnification.
Figure 9:
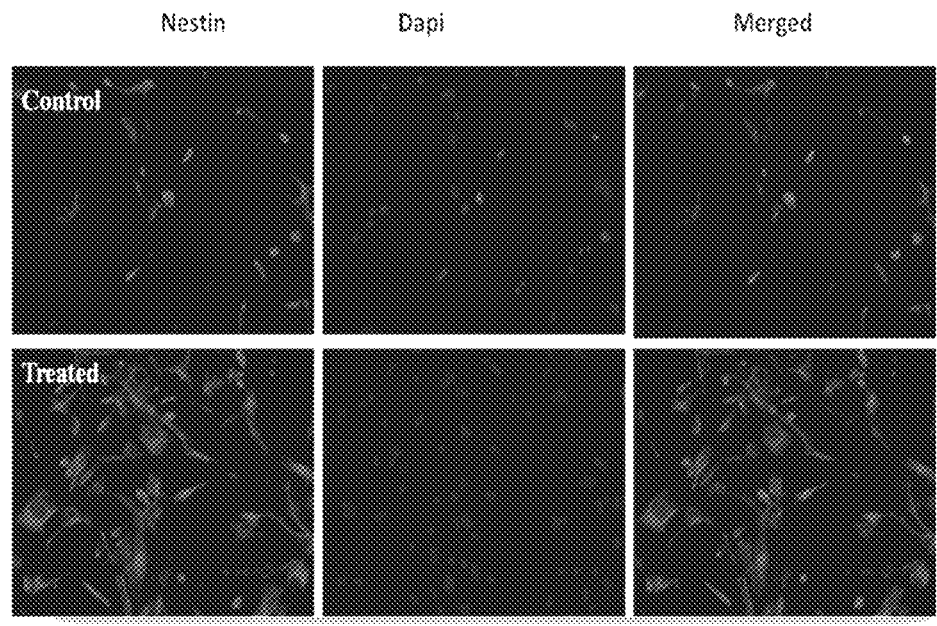
Figure 10:
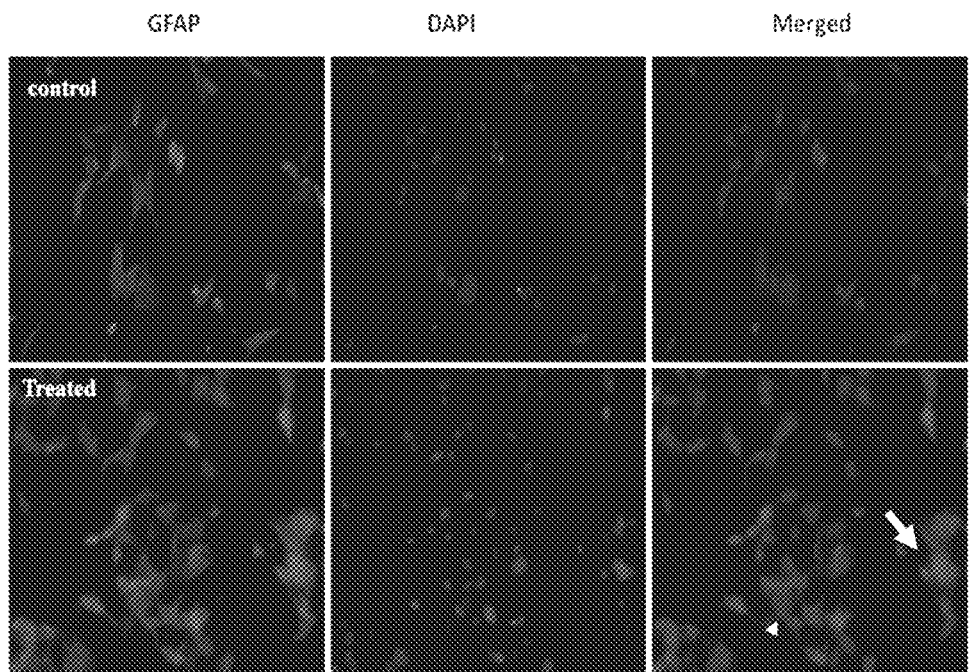
FIG. 10 depicts representative images showing GFAP expression in isoxylitones treated (A) cortical and (B) CoCul-CTX cells. Cells were treated with isoxylitones and following 24 h followed by immunostaining to assess the intensity of GFAP protein expression. Images were analyzed using ImageJ software. The arrow shows a prominent increase of GFAP expression in treatment group as compared to vehicle control. The nucleus was stained with DAPI.
Figure 10:
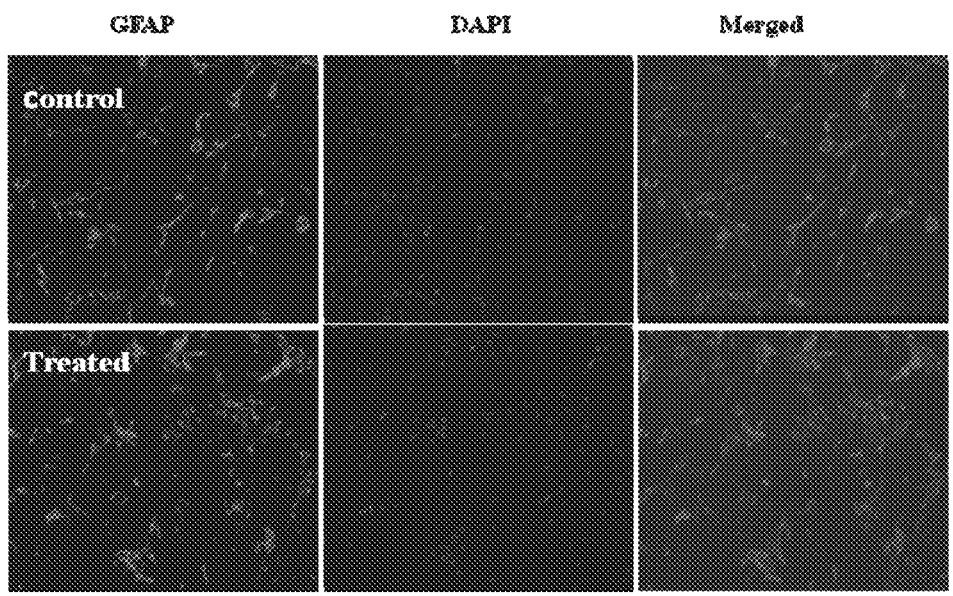
Figure 11:
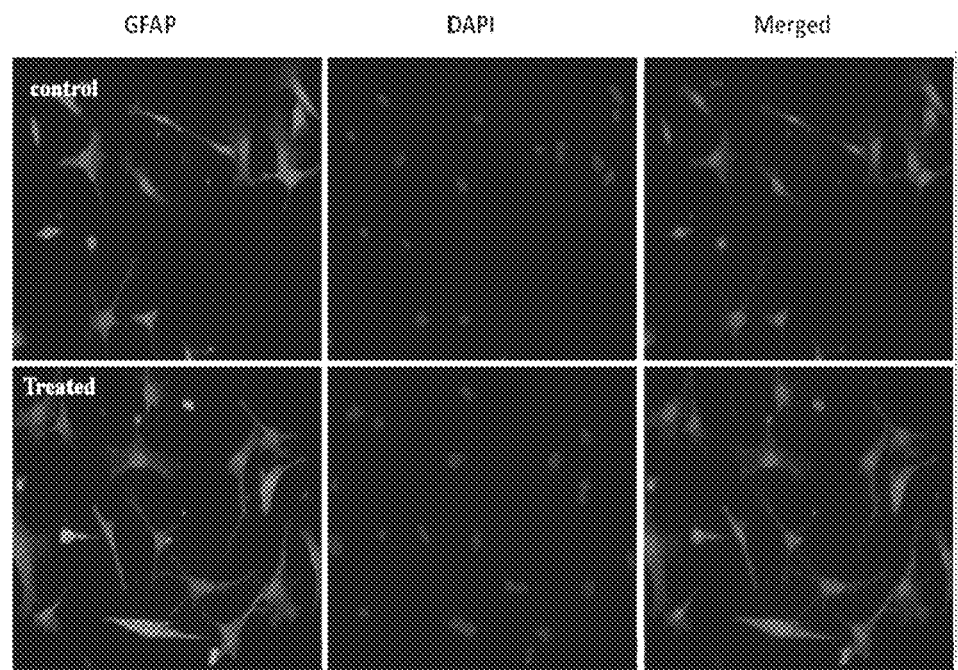
FIG. 11 depicts photomicrographs representing Immunochemistry of GFAP in (A) hippocampal and (B) CoCul-HP cells after treatment with isoxylitones. Neurons of hippocampus were treated at the dose of isoxylitones (150 µg/ml) for 24 h and to detect the expression of nestin protein in treated cultures immunocytochemistry was used and microscopy was done with Nikon 90i microscope. No significant difference in intensity of taken images was found in treated cells as compare to control cells
Figure 11:
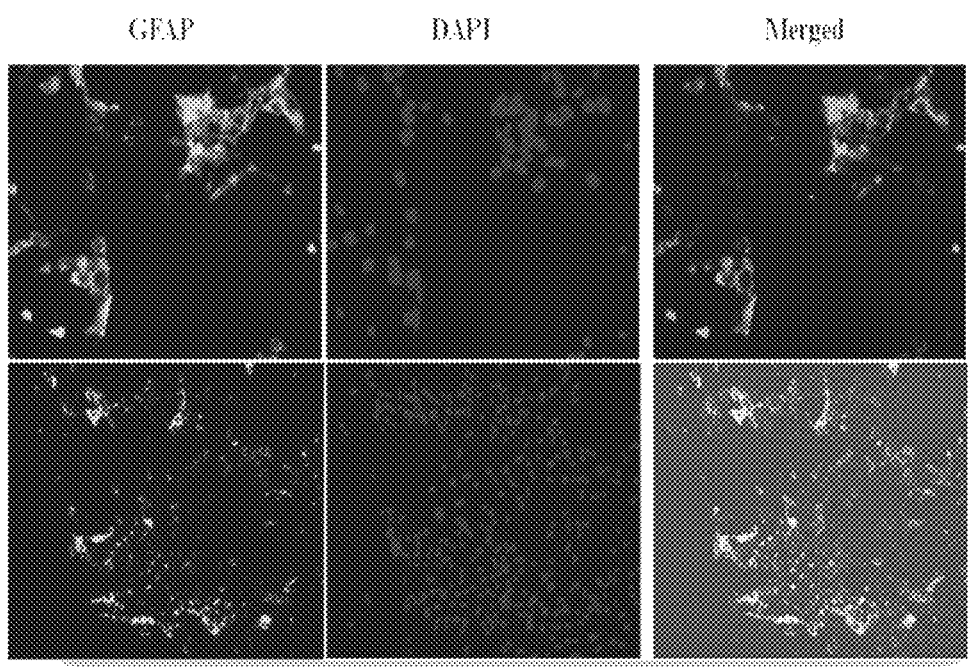
Figure 12:
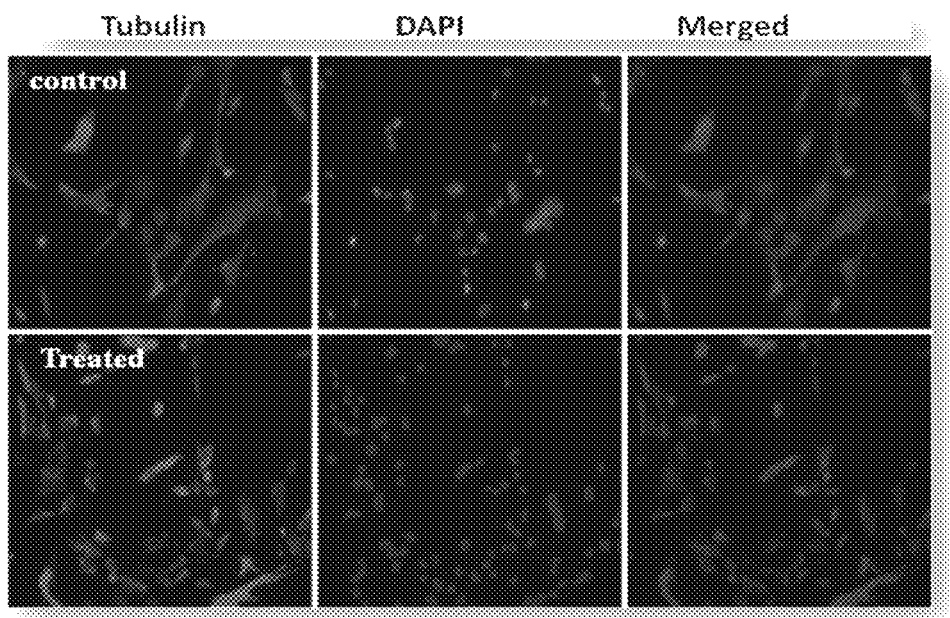
FIG. 12 depicts expression of tubulin following treatment with isoxylitones in (A) cortical and (B) CoCul-CTX cells. The representative photomicrographs showing a prominent immunofluorescence of tubulin in treated cortical cells indicating a significant upregulation of tubulin (P<0.01). The images were taken on Nikon 90i microscope with 20× magnification and analyzed on ImageJ software. DAPI (blue) was used for staining of nuclei.
Figure 12:
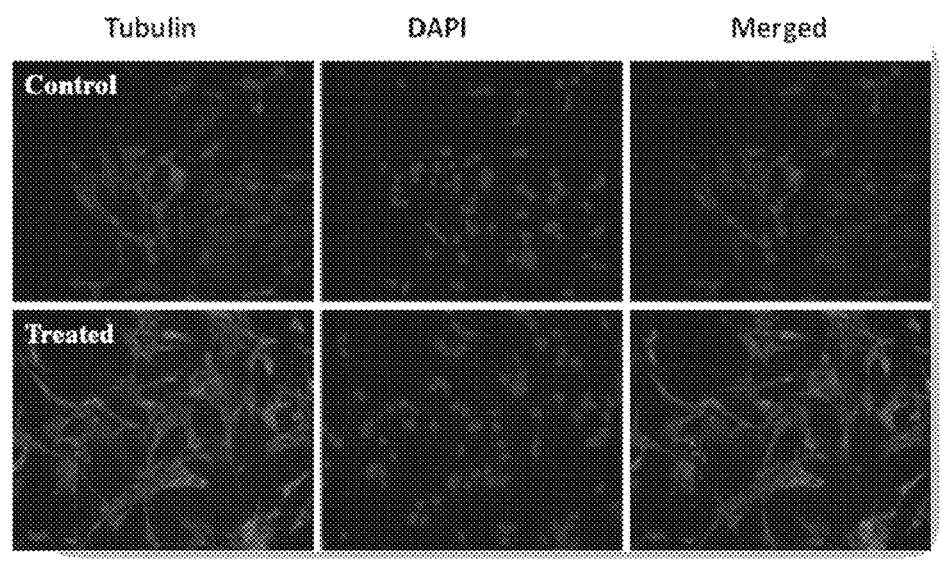
Figure 13:
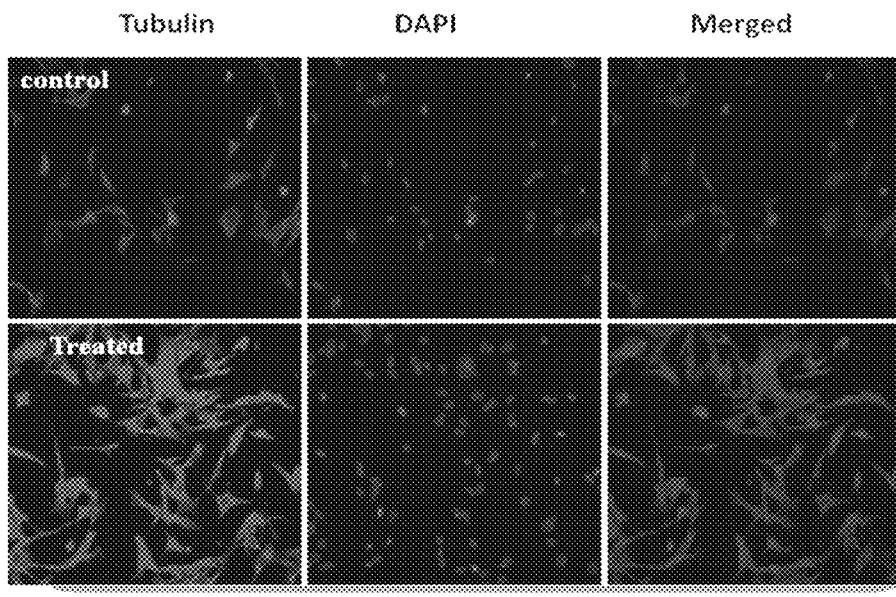
FIG. 13 depicts isoxylitones treated (A) hippocampal and (B) CoCul-HP cells showing tubulin expression. Hippocampal neurons were treated with 150 µg/ml of isoxylitones for 24 h and then immunostained with tubulin antibody. Images were captured on 90i Nikon microscope with magnification of 20×. Images showing significant upregulation in treated cultures as compare to control cells.
Figure 13:
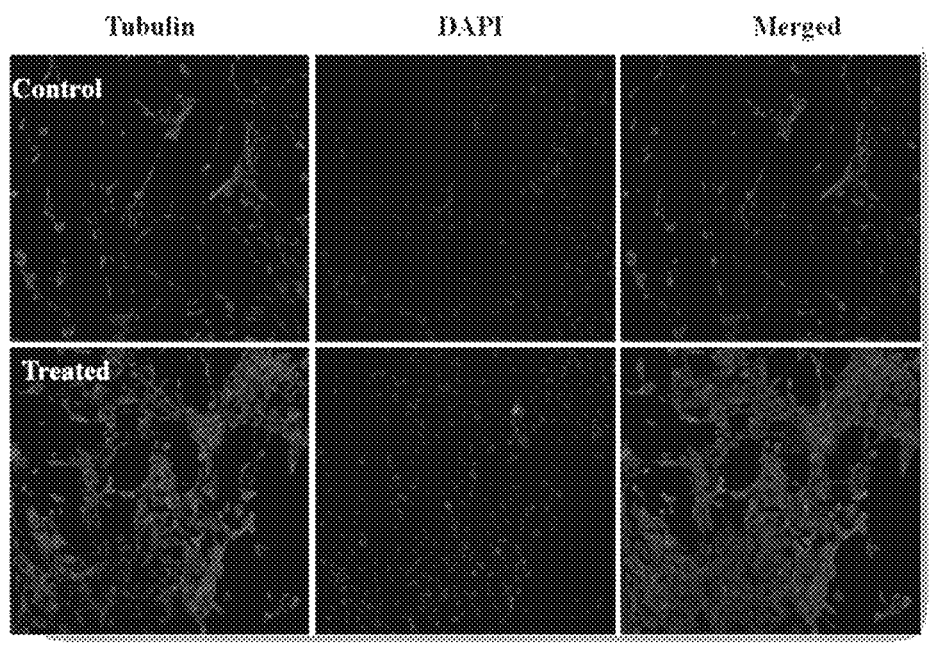
Figure 14:
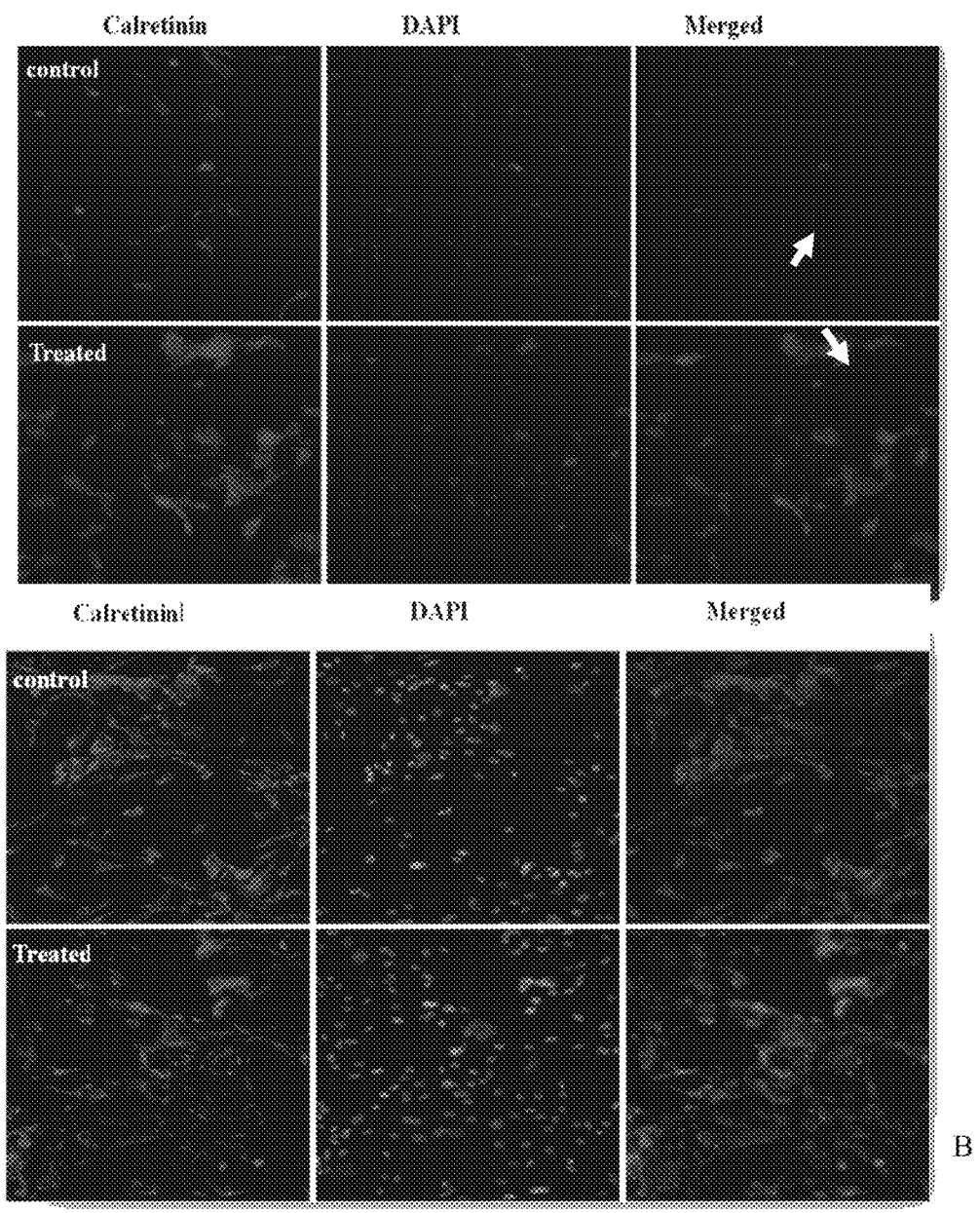
FIG. 14 depicts photomicrographs of Calretinin (CR) immunoreactive (A) cortical and (B) CoCul-CTX cells with and without ISO [E/Z] treatment. The immunofluorescence staining for CR protein was done using cultured cortical cells from 2-3 days old rat pups after treatment with isoxylitones. DAPI staining was used to reveal the total number of nuclei. The arrows show prominent increase in the fluorescent intensity of calretinin in the treated group as compared to control cells.
Figure 15:
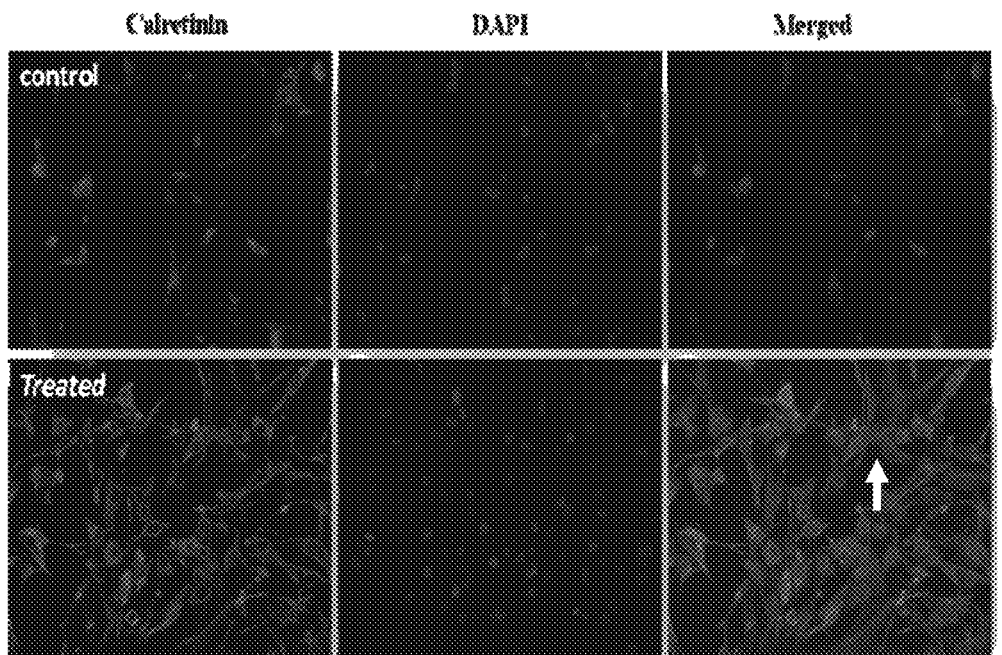
FIG. 15 depicts the effect of isoxylitones on CR expression in (A) hippocampal and (B) CoCul-HP cells. Photomicrographs representing immunoreactivity of CR in isoxylitones treated cells. Imaging was done under 90i microscope showing significant increase in CR expression as compare to control group after treating the cells with isoxylitones. DAPI was used to stain the number of nuclei (blue).
Figure 15:
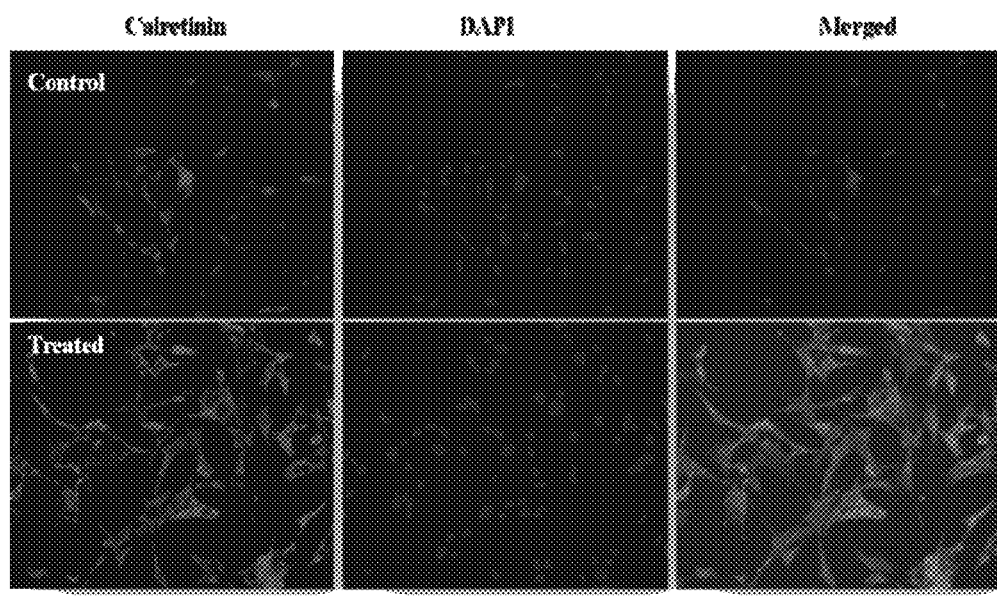
Figure 16:
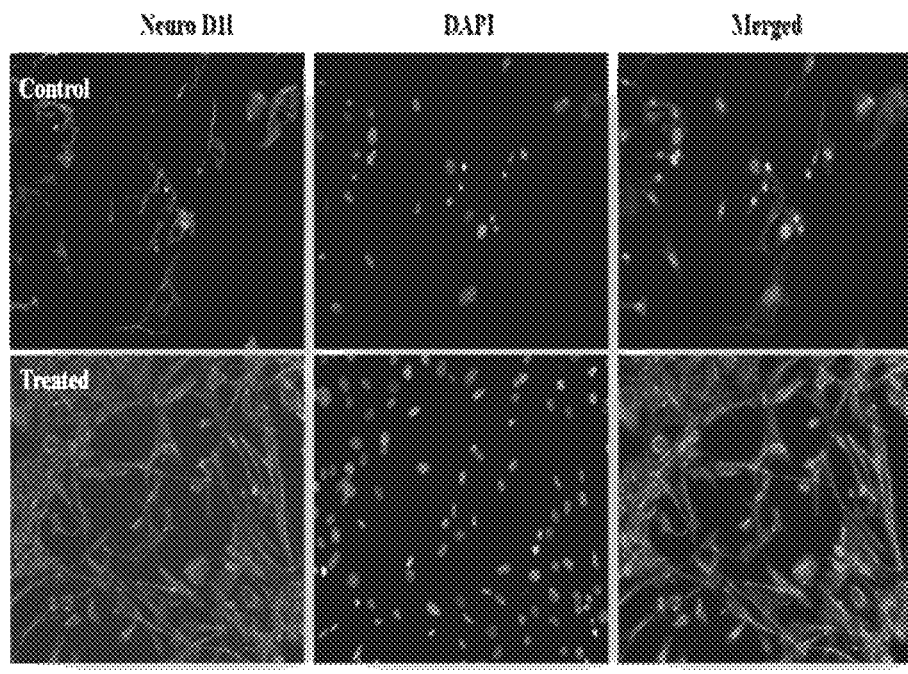
FIG. 16 depicts Neuro D1 protein expressions in (A) cortical and (B) CoCul-CTX cells following the treatment with isoxylitones. The cortical cells were treated with isoxylitones for 24 h at the dose of 150 μg/ml. The untreated cells were kept as a control group. To observe the expression of Neuro D1 protein in control and treated cultures immunocytochemistry was performed using anti-Neuro D1 antibody. Images were captured using 90i Nikon microscope at magnification of 20×. Images showing significant upregulation in treated cultures as compare to control cells.
Figure 16:
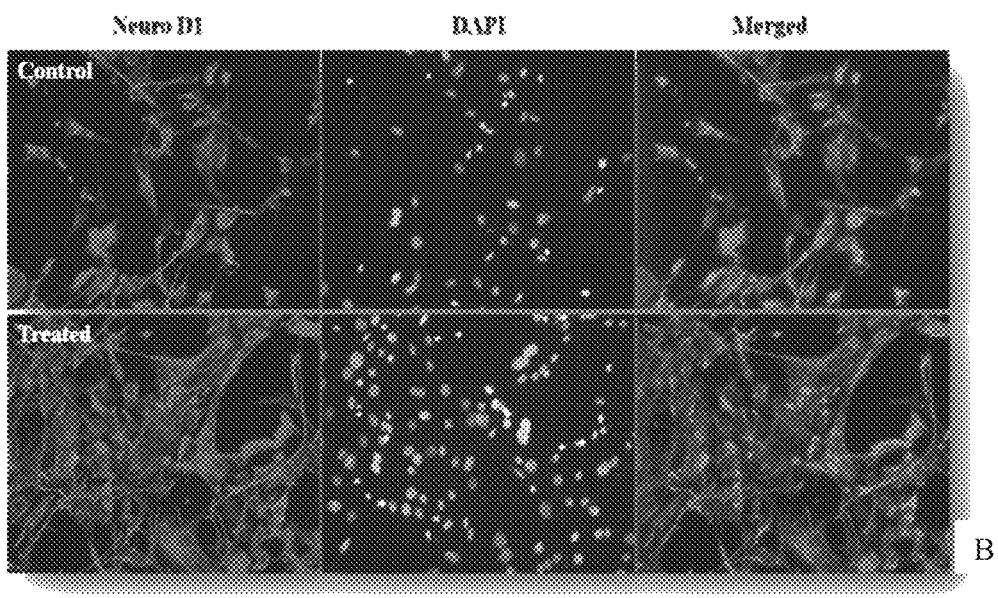
Figure 17:
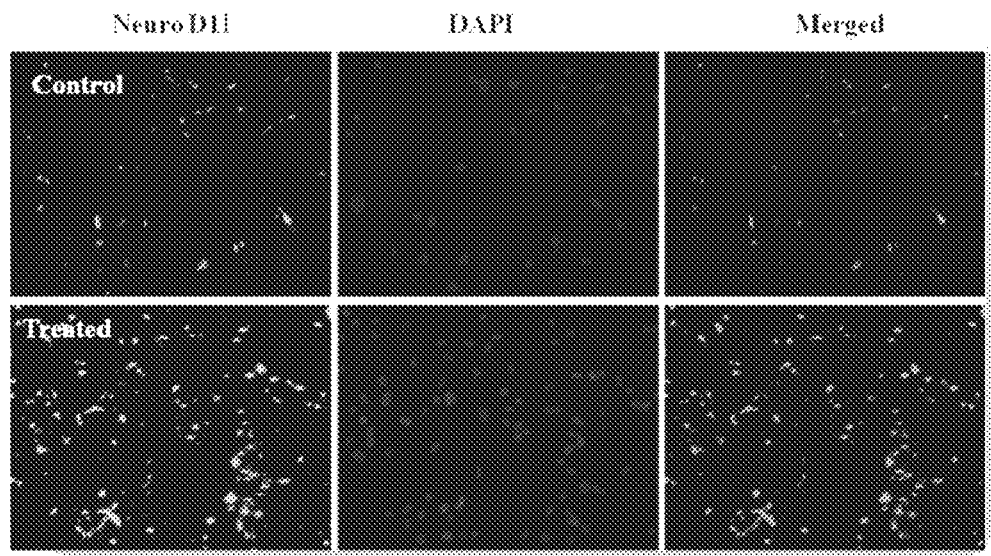
FIG. 17 depicts immunostained images of (A) hippocampal and (B) CoCul-HP cells showing Neuro D1 after isoxylitones treatment. A significant up-regulation in immunofluorescence of NeuroD1 intensity in hippocampal neurons can be seen in the isoxylitones treated cells. The nuclei were stained with DAPI (blue). The images were captured at 20× magnification.
Figure 17:
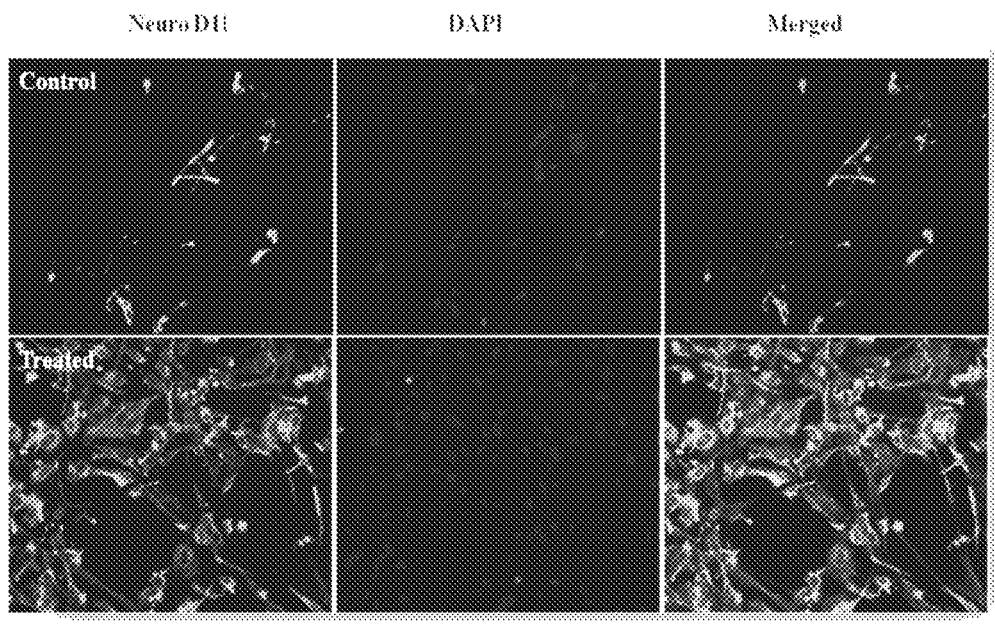
Figure 18:
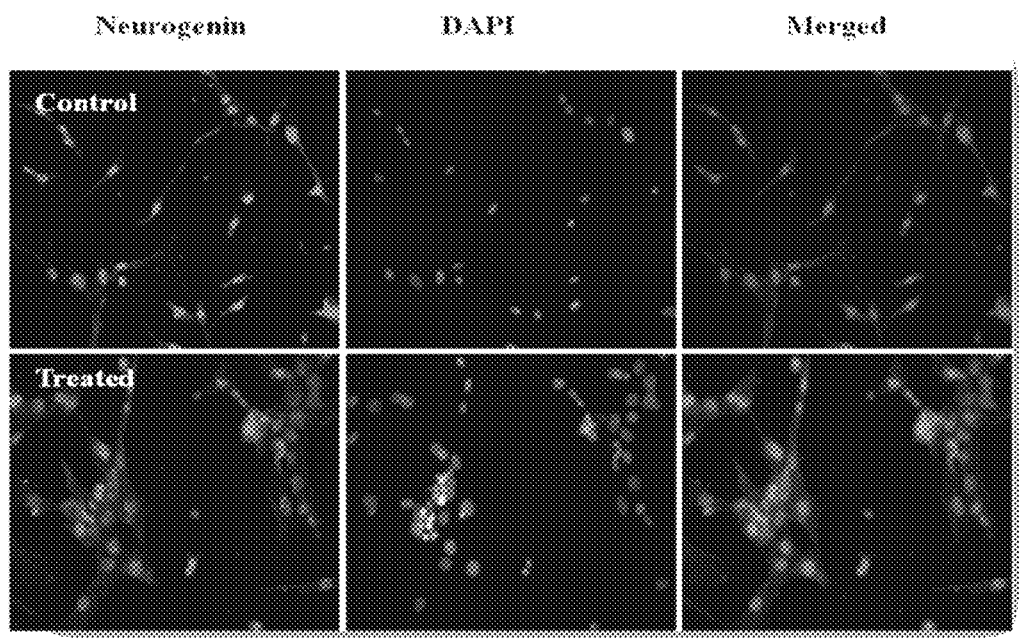
FIG. 18 depicts immunocytochemical analysis of neurogenin expression in isoxylitones treated (A) cortical and (B) CoCul-CTX cells. Representative images showing expression of neurogenin in cortical cells after treatment with isoxylitones. Immunostaining shows prominent neurogenin expression (arrow) in treated cells. Images were taken using 90i microscope at 20× magnification.
Figure 18:
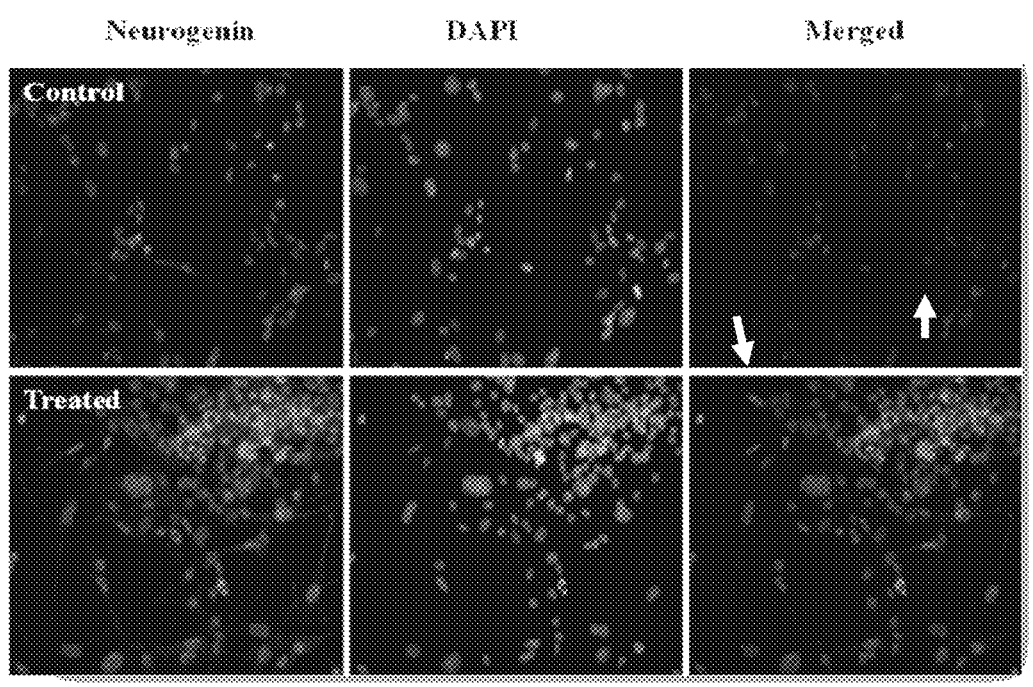
Figure 19:
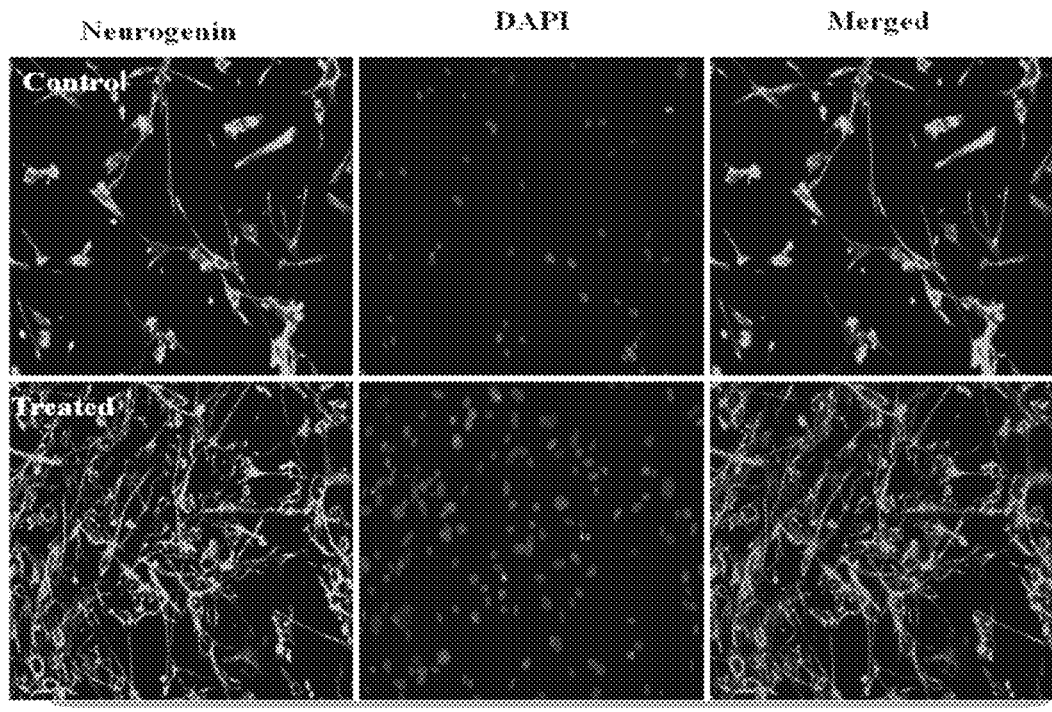
FIG. 19 depicts the representative images showing expression of neurogeninin in (A) hippocampal and (B) CoCul-HP cell cultures following treatment with isoxylitones. Arrow shows elevated neurogenin expression in hippocampal cells treated with isoxylitones for 24 h. Increase in the neurogenin expression was significantly different from the control group (P<0.001). Images were captured at 20× magnification. The stain the nuclei DAPI (blue) was used.
Figure 19:
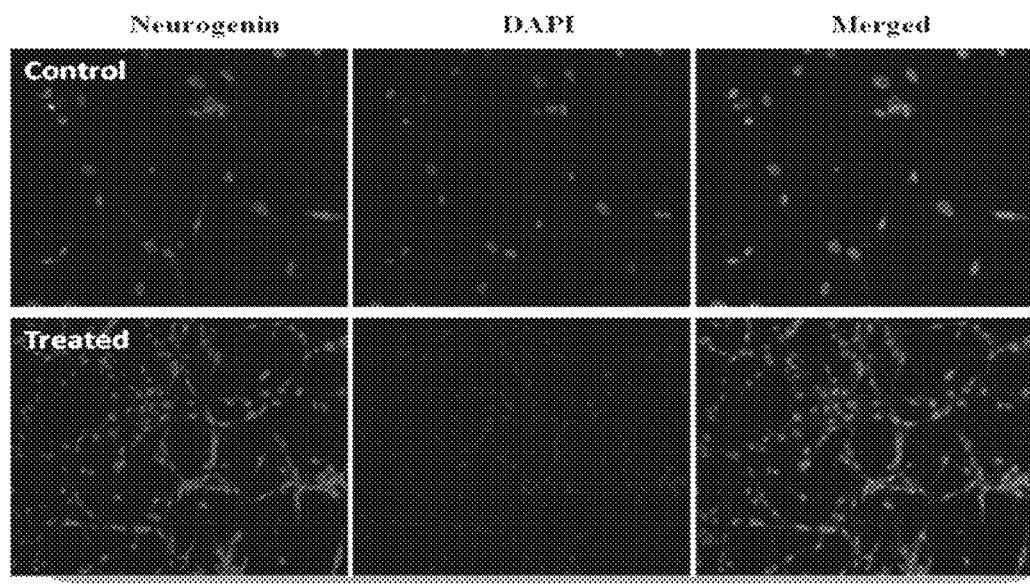

The present disclosure provides the methods for detecting neurogenesis effects of isoxylitones on the cortical and hippocampal cells either cultured alone or cocultured with bone marrow stromal cells (BMSCs). It also describes the methods for the production of neurologic component for promoting the neurogenesis.

Here, the neurogenesis term is used to refer the differentiation and proliferation of the neural cells from the progenitor cells in vitro. The extent of neurogenesis was determined by a variety of techniques such as observing morphological changes in the cells using microscopic techniques. The neurogenesis was further determined by cellular biomarkers which indicates the neurogenesis such as nestin, GFAP, β-III tubulin, calretinin, neuroD1 and neurogenin.

A compound that modulates neurogenesis is referred as neuromodulator. Compounds with neurogenesis modulating effects are considered as advantageous as they can promote and support early brain development and can also be used in treating neurodegenerative diseases or injuries. In the present invention isoxylitones were discovered as neuromodulators promoting the neurogenesis of both the hippocampal and cortical cells.

The method determines the culturing of the cortical and hippocampal cells in absence of the isoxylitones and then compared with the cultures grown in the presence of the isoxylitones in order to determine the extent of neurogenesis. A significant increase in the neurogenesis in the treated cultures indicates the neurogenesis promoting effect of the compound.

The method also further provided a control in which the cortical and hippocampal cells were cocultured with BMSCs. The BMSCs are reported to produce the different lineage of cells and also express the characteristics of the cells with which they are cocultured. These cells were then compared with the cortical and hippocampal cells cultured alone and in the presence of the isoxylitones to confirm the extent of neurogenesis without having influence from the BMSCs.

During neurogenesis, the isoxylitones differentiate the neuronal precursor cells, neuronal cells, and cells having neuronal properties. The morphological changes as well as immunocytochemical studies were performed to determine the extent of neurogenesis.

Methodology

Animals:

Adult Wistar rats (100-120 g) and two days old Wistar pups raised in the breeding colony at International Center for Chemical and Biological Sciences, University of Karachi, were used. In the present study, Animal care and experimental protocols were conducted in accordance with the ethical guidelines set by the Scientific Advisory Committee on Animal Care, Use, and Standards, International Center for Chemical and Biological Sciences (ICCBS).

Compound Preparation:

The test compounds isoxylitones (E/Z)-(1-(3,5,5-trimethylcyclohex-2-enylidene)propan-2-one and corresponding acid analog (E/Z)-2-(3,5,5-trimethylcyclohex-2-enylidene) acetic acid were dissolved in 0.9% NaCl. Stock solutions of 1000 μg and 2000 μg/mL were prepared. The stock solutions were made freshly for each experiment and treated within 30 minutes. The working solutions of the compound were prepared from stock solutions by diluting these in the culture medium. Five different working concentrations of compounds i.e., 25 m/mL, 50 m/mL, 75 m/mL, 100 μg/mL, and 150 μg/mL were used to treat the cells.

Isolation and Culture of Hippocampal and Cortical Neurons:

For isolation of hippocampal and cortical neurons, two days old rat pups were sacrificed under sterile conditions. Brain samples were carefully isolated and hippocampal and cortical regions were dissected out and placed in ice-cold PBS supplemented with 1% penicillin-streptomycin. Tissue was chopped in small pieces with a sterile scalpel and washed three times with PBS. Subsequently tissues were digested in typsin-EDTA solution (0.05% of trypsin) for 7 minutes at 37° C. and 5% $CO_2$ in a humidified chamber. After typsinisation, cells were washed three times in Dulbecco's Modified Eagle's Medium (DMEM) media containing 5% FBS and finally triturated using flame-polished Pasteur pipette to prepare dissociated cell suspension. The cell suspensions were then centrifuged at 1200 rpm for 4 minutes, supernatants were discarded and cell pellets were re-suspended in 1 mL complete media to find out the cell count and viability. Cells were finally cultured in DMEM (high glucose), supplemented with 10% fetal bovine serum (FBS), 1% L-Glutamine, 1% penicillin/streptomycin (10,000 U/mL and 10 mg/mL, resp.), and 1% sodium pyruvate. The culture flasks (75 cm$^2$) were then incubated at 37° C. with 5% $CO_2$. Cells were examined daily for any change in morphology or contamination. Media was changed twice or thrice weekly. All cell work was done in a tissue culture hood under sterile conditions.

Passaging of Cultured Cells:

Once the cells were confluent ~70 to 80%, media was aspirated and the cells were washed with phosphate buffer saline (PBS) pH 7.4, treated with 2 mL of 0.05% trypsin-EDTA solution for 3 minutes incubated at 37° C. After incubation, cells were observed under microscope to check the detachment of the monolayer from the flask. Complete media (7 mL) was then added to flask to deactivate the trypsin and the cell suspension was transferred to 15 mL falcon tube. Cells were centrifuged at 1200 rpm for 4 minutes, supernatant was discarded; cells were re-suspended, split and one portion was cryopreserved for further use.

Cell Counting and Cell Viability Using Trypan Blue Exclusion Test:

Trypan Blue Exclusion Test of cell viability was used to determine live cells/mL in freshly prepared cell suspension before seeding the cells. Viable cells exclude the dye while non-viable cells are colored dark blue. Briefly, cell suspension was diluted 1:1 with 0.4% trypan blue in physiological saline (0.15M NaCl) and thoroughly mixed. The suspension was loaded into both counting chambers of the hemacytometer, and the cells were counted under microscope at 20× magnification. The cells were counted in corner square consisted of sixteen small squares.

Number of viable cell/mL=total number of viable cells counted×$10^4$×trypan blue dilution.

Percentage of viable cells was calculated by using the formula:

$$\% \text{ viable cells} = \frac{\text{Number of cells excluding dye}}{\text{Total number of cells counted}} \times 100$$

Isolation of Bone Marrow Stromal Cells and Co-Culturing with Hippocampal and Cortical Cells:

Wistar rats (150-200 gm) were used to isolate bone marrow (BM). Rats were sacrificed and their femurs were removed aseptically. The bone marrow (BM) was flushed from the shaft of the bone by clipping of the epiphysial ends and flushing using a 26-gauge needle with ~2 ml of Dulbecco's Modified Eagle's medium (DMEM) supplemented with 5% FBS, 1% penicillin/streptomycin solution, 1% sodium pyruvate and L-glutamine. The BM was then centrifuged for 8 minutes at 1000 rpm. Following centrifugation, cell pellet was collected and 1 ml of fresh DMEM was added. The cell viability was checked using trypan blue exclusion method. The cells were then divided into three equal parts. One part was co-cultured with freshly isolated hippocampal cells in T75 cm$^2$ flask, 2$^{nd}$ with freshly isolated cortical cells and the third portion (BM cells only) was cultured as a control. The cell density for co-cultures was set at 140,000 cells/ml for each type of culture. The cultured flasks were then incubated at 37° C. and 5% CO2. After 4-5 days, floating hematopoietic cells and dead debris/tissues of hippocampus and cortex were removed and bone marrow stromal cells (BMSCs) were recovered due to their tendency to adhere. Medium was replaced after every 3 to 4 days till cells became 80-90% confluent.

To obtain passage 1 (P1 cells) culture, sub-culturing was performed at 80-95% confluency. Following aspiration of medium, cells were washed with 1× phosphate buffer saline (PBS). For cells detachment, 2 ml trypsin-EDTA (0.05%) solution was added (2 ml for T75 tissue culture flasks). Cultures were allowed to incubate at 37° C. for 4 minutes. Complete detachment was confirmed through phase contrast microscope (Nikon, Japan). The action of trypsin was neutralized by adding equal volume of DMEM medium. Cell suspension was collected in 15 ml falcon tube and centrifuged at 1000 rpm for 8 minutes. The resultant cell pellet was re-suspended in 2 ml fresh medium and equally distributed in two T75 flasks containing 10 ml of fresh complete medium. The flasks were labeled and incubated at former conditions in incubator. Medium was changed every 3-4 days until confluent growth was observed.

In Vitro Screening of Compounds for Cell Proliferation Activity

The Tetrazolium MTT [3-(4, 5-dimethyl thiazol-2-yl)-2, 5-diphenyl tetrazolium bromide] Assay: MTT assay was used to screen various compounds for their proliferating effect on cortical cells and hippocampal cells. The principle of MTT test is based on the ability of live cells to form insoluble purple formazan product from the breakdown of the water soluble yellow tetrazolium salt by mitochondrial enzyme succinate dehydrogenase (Mosmann, 1983). The resulting intracellular purple formazan can quantify by spectrophotometric means. The MTT Cell Proliferation Assay measures the cell proliferation rate and conversely, when metabolic events lead to apoptosis or necrosis, the reduction in cell viability.

The density of the cortical and hippocampal cells was adjusted at the density 2×$10^5$ cells/mL in complete DMEM medium (5% FBS). The cells (5000/well) were then plated in 96-wells plate and incubated for 24 hrs at 37° C. with 5% $CO_2$. Following 24 hrs incubation, media was removed and 100 µL of each test compounds in DMEM media (5% FBS) were added. Care was taken for the compounds soluble in DMSO such that DMSO concentration does not exceed above 0.1%. The culture plates were re-incubated for 24 hrs at 37° C. in 5% $CO_2$. Cells treated with 0.1% DMSO in complete media (5% FBS) were used as vehicle controls. The same volume of medium without cells was used as blank. After incubation, sample solution in the wells was aspirated and 100 µL of 0.5 mg/mL MTT dye (Promega Corporation, WI, USA) was added to each well and incubated at 37° C. in 5% $CO_2$ for 3 hrs. After 3 hrs incubation, medium was removed and 100 µL of DMSO was added to each well. The plates (covered with aluminum foil to protect the crystals from light) were shaken on an orbital shaker for 30 min to solubilize the formazan crystals. The absorbance was read at 495 nm on spectrophotometer. The percentage of viable cells following treatment was normalized to vehicle control. All assays were done in triplicates at least three times. The percent rate of proliferation was calculated using the following formula, $$\% \text{ rate of proliferation} = \{(At-Ab)/(Ac-Ab)\} \times 100$$

Where,

At=Absorbance value of test compound (cells+media+drug)

Ab=Absorbance value of blank (media+drug)

Ac=Absorbance value of control (cells+media+Vehicle)

Data was analyzed using SPSS (19), and graphs were made on Excel.

Since out of all tested compounds, we observed a significant potent activity of isoxylitones followed by acid analog on the cell proliferation. The subsequent sections describe the detailed studies of isoxylitones on various neurogenic markers.

Growth Supporting Effect of Isoxylitones on Neuronal Cultures:

To evaluate the growth supporting effect of isoxylitones the hippocampal, cortical and co-cultured cells were plated in 6-well plates and treated with 25 µg/mL, 50 µg/mL, 75 µg/mL and 150 µg/mL doses of isoxylitones. Cells with no treatment were set as a control. The plates were incubated for 24 and 72 hrs in a humidified chamber at 37° C. in 5% $CO_2$. To assess the morphology of the treated cells, images were captured and digitalized with Nikon TE-2000 inverted microscope equipped with phase-contrast optics to measure the difference of control group from treated group. The cells were observed carefully in order to check if they maintain their morphological characteristics after treatment with the compound. The doses which supported the maximum proliferation were used for proliferation assays i.e., AlamarBlue and BrdU assay.

AlamarBlue Assay:

AlamarBlue (AB), a water-soluble dye having resazurin salt was used to evaluate the effect of isoxylitones on the proliferation of the cultured cells. AB measures mitochondrial reductase activity of live cells. The resazurin has ability to enter the cytosol of viable cell and converted to the reduced fluorescent form resorufin by mitochondrial enzyme activity by accepting electrons from NADPH, FADH, FMNH, NADH as well as from the cytochromes. The redox reaction is accompanied by a change in color of the culture medium from blue to fluorescent red (Al-Nasiry, Geusens, Hanssens, Luyten, Pijnenborg, 2007). The amount of fluorescence produced is proportional to the number of living cells (Al-Nasiry, Geusens, Hanssens, Luyten, Pijnenborg, 2007). The cultured hippocampal, cortical and co-cultures were plated in 96-well plates (10,000 cells/well) and incubated for 24 hrs at 37° C. and 5% $CO_2$. Next day, cells were treated with varying concentrations of isoxylitones i.e., 25 µg/mL, 50 µg/mL, 75 µg/mL, 100 µg/mL and 150 µg/mL. The plates were re-incubated for 24 hrs at 37° C. and 5% $CO_2$. Following incubation, 10% of AB (v/v) i.e., 20 µL was added directly in each well and incubated for 4 hrs at 37° C. in a 5% $CO_2$ incubator. As negative control, alamarBlue dye was added to the medium without cells. After incubation, the fluorescence intensity in each well was recorded at an excitation wavelength of 570 nm and an emission wavelength of 600 nm. The rate of cell proliferation was expressed as the relative fluorescence intensity. For alamar Blue data analysis, a single blank was run each time the analysis done. The blank media fluorescence measurement was subtracted from fluorescence measurements of cells from the same run.

Formula used to calculate the percentage reduction of AB using absorbance readings:

$$\% AB \text{ reduction} = \frac{(O2 \times A1) - (O1 \times A2)}{(O2 \times P1) - (O1 \times P2)} \times 100$$

Where:

O1=molar extinction coefficient (E) of oxidized alamarBlue® (Blue) at 570 nm

O2=E of oxidized alamarBlue® at 600 nm

A1=absorbance of test wells at 570 nm

A2=absorbance of test wells at 600 nm

P1=absorbance of positive growth control well (cells plus alamarBlue® but no test agent) at 570 nm P2=absorbance of positive growth control well (cells plus alamarBlue® but no test agent at 600 nm BrdU-Incorporation Assay: For measuring the newly synthesized cells during proliferation of treated and un-treated cultured hippocampal, cortical and co-cultured cells, the BrdU (Calbiochem®, CA, USA) cell proliferation ELISA kit was used. This immunoassay is based on the measurement of BrdU (5-bromo-2'-deoxiurydine) incorporation into DNA during division phase of the proliferating cells. For BrdU proliferation assay, primary cultured cells were grown in 75 cm flasks and when cells were confluent they were trypsinized and re-plated with a cell density of 1×105 cells/mL in 96-well tissue culture grade flat bottom ELISA plates, i.e., (10,000 cells/well) in DMEM medium (high glucose). The plates were incubated overnight at 37° C. in 5% CO2. Next day, media was changed and adherent cells were treated with different doses of isoxylitones, i.e., 25, 50, 75, 100, and 150 µg/mL and incubated for 24 hrs in a humidified chamber at 37° C. and 5% CO2.

The following day, the cells were first labeled by the 20 µL of BrdU (1:2000) in fresh medium and kept in a humidified atmosphere at 37° C. for 24 hrs. During 20-24 hrs of labeling period, BrdU is incorporated in place of thymidine into the DNA of the proliferating cells. After removing the labeling medium by tapping off the plate, cells were fixed, and DNA denatured in one step by adding 200 µL of fixative or Denat solution (provided in the kit) in each well following incubation for 30 minutes at room temperature.

The fixation and denaturation of DNA is required to expose the incorporated BrdU for detection by the antibody. The fixative or Denat solution was removed by flicking off and tapping on paper towel. For BrdU immunolabeling, 100 µL of diluted 100× anti-BrdU (1:100 in dilution buffer) was added in each well, in order to locate and bind to the BrdU incorporated into the newly synthesized cellular DNA, the plates were incubated for 1 hr at room temperature. Following incubation, the plates were washed gently three times with 1× wash buffer (25 ml of 20× concentrated solution added to 475 ml deionized water). After washing, 100 µL of peroxidase goat anti-mouse IgG HRP conjugate (diluted in 1×PBS and filtered through 0.24 µm syringe filters) was added into each well and incubated for 30 minutes at room temperature. The conjugate was washed gently three times with 1× wash buffer. To reduce the background and increase precision further, washing was done by flooding the entire plate with deionized $H_2O$. After removing content of well by inverting or tapping on paper towel, 100 µL of substrate solution was added into each well and incubated in dark at room temperature for 15 minutes. The reaction was stopped by adding stop solution in each well for ten minutes. The immune complexes were detected by the subsequent substrate reaction and the absorbance was measured on spectrophotometer plate reader at dual wave lengths of 450-595 nm within 30 minutes of adding the stop solution. The data was analyzed using SPSS and graphs were made on Excel.

Immunocytochemical Analysis of Primary Cultured and Cocultured Cells:

Immuncytochemical analysis was performed for differentiation studies of primary cultures of cortex, hippocampus, and co-cultures (CoCul) in absence of growth factors and serum free medium. Characterization of neuronal markers was observed in both treated and non-treated cells using immunofluorescence staining.

The cultured cells of cortex, hippocampus, and co-cultured cells in the presence of serum free medium were plated Briefly, 5 different regions were randomly selected and the fluorescence intensity was quantified in cells and the background intensity of each image was subtracted from it, the residual particles were measured to represent expression of relevant protein. Cells or fields were counted and percentage intensity of protein expression was measured and means percentage intensity was calculated. Data from three individual experiments was obtained and expressed as means±SEM.

TABLE 2.1

Primary and secondary antibodies used for immunochemical staining

| Markers | Primary Antibodies | Dilution of Primary Antibodies | Secondary Antibodies |
|---|---|---|---|
| CALRETININ | Polyclonal goat IgG AF5065 | 8-25 μg/ml | AlexaFlour ®$^{546}$ Donkey anti goat IgG (H + L) |
| GFAP | Poly clonal sheep IgG AF2594 | 5-15 μg/ml | Donkey anti-Sheep IgG (H + L) |
| NESTIN | Monoclonal mouse IgG2A MAB2736 | 8-25 μg/ml | Alexa Flour ®$^{488}$ Goat anti-rabbitt IgG (H + L) |
| NEUROD1 | polyclonal goat IgG AF2746 | 5-15 μg/ml | Alexa Flour ®$^{546}$ Donkey anti-goat IgG (H + L) |
| NEUROGENIN | Mouse monoclonal IgG MAB3314 | Alexa Flour ®$^{546}$ Goat anti-mouse IgG (H + L) | 8-25 μg/ml |
| TUBULIN(anti Tuj-1) | Monoclonal mouse IgG2A, MAB 1195 | Alexa Flour ®$^{546}$ Goat anti-mouse IgG (H + L) | 8-25 μg/ml | in chamber slides at the density of 20,000 cells/mL and treated with a proliferative dose of isoxylitones, i.e., 150 μg/ml for 24 hrs at 37° C. and 5% $CO_2$ to let the cells adhere on the bottom surface of the slide. Following incubation, the media was refreshed and the cells were immunolabelled as mentioned in table #2.1.

For immunostaining, the media was removed; cells were washed gently with 1 mL of 1×PBS. After removing 1×PBS, 4% formaldehyde was added and the slides were incubated for 20 minutes at room temperature to fix the cells. The fixative was aspirated followed by a three times rinse with 1 mL of 1×PBS. After washing, the blocking buffer (BSA having 3% normal goat serum, 0.2% tween-20 and 0.3% of Triton X-100 in 10×PBS) was added and the slides were kept at room temperature for an hour. Then, the cells were washed gently three times with 1×PBS on an orbital shaker and 300 μL of primary antibodies (dilution mentioned in table #2.1) were added to each slide and incubated overnight at 4° C. Following incubation, the cells were washed gently in PBS three times (5 minutes each wash) on an orbital shaker. Next secondary antibody (Table #2.1) in 3% normal serum or BSA was added to their respective chamber and incubated for 1 hour at room temperature in dark. Following incubation, the slides were washed with 1×PBS.

Image Analysis:

Diluted Dapi (1:1000) was added into each slide to counter stain the nucleus. After rinsing twice with distilled water, images were captured using the Nikon 90i with fluorescence microscopes (Nikon. Tokyo, Japan) equipped with Nuance Software version 3.1 (Caliper Life Sciences. Hopkinton, Mass.). The magnification used was 20×.

For quantification studies, ImageJ software (National Institutes of Health, USA) was used to digitalized the images. This software provides multiple imaging system data comparisons taking densitometry in consideration.

In—Vitro Model of Hypoxic Pre-Conditioning:

In-vitro model of hypoxic cells was established by hypoxia chamber, which contain 5% carbon dioxide, 1% oxygen and 94% nitrogen. Isolated cortical and hippocampal cells from 1-2 days old rat pups were cultured in 75 cm flask in DMEM medium, after culturing cells were plated on 96 well plate at 7000-8000 viable cells per well and incubated in hypoxia chamber for 2 hour at 37° C. for hypoxic conditioning or oxygen deprivation. Following hypoxic shock, medium was replaced with fresh complete medium. Only cells without hypoxia were kept in normal condition as a control group while untreated hypoxic cells were kept as a positive control cells. Following two hours hypoxia the treatment of isoxylitones at various doses was given to hypoxic cells and MTT assay was used to determine the viability of cells in all treated and control cells. The absorbance of the plate was read by spectrophotometer at 570 nm wavelength.

Statistical Analysis:

Statistical analysis was carried out using SPSS and one-way ANOVA. A P-value of <0.05 was considered significant. To determine the intra- and inter-assay variability, data from three consecutive experiments were analysed with application of Posthoc Bonferoni's test for multiple comparisons.

What is claimed is:

1. A method for activating transcription genes NeuroD1 and Neurogenin (Ngn) in cortical, hippocampal and neural progenitor cells to treat patients suffering from cerebral ischemia, Alzheimer's disease, Parkinson's disease, or traumatic brain injury, by exposing said cells to a therapeutically effective amount of isoxylitones ((E/Z)-1-(3,5,5-trimethyl-2-cyclohexen-1-ylidene) propan-2-one), the acid analog (E/Z)-1-(3,5,5-trimethyl-2-cyclohexen-1-ylidene) acetic acid, or a salt thereof.

2. The method of claim 1, wherein the activation of transcription genes results in differentiation and proliferation of the said cells.

3. The method of claim 2, wherein the action of the transcription genes results in expression of cortical neurons.

4. The method of claim 2, wherein differentiation continues after removing the cells from exposure to a compound of claim 1.

\* \* \* \* \*